(12) United States Patent
Chen

(10) Patent No.: US 10,472,601 B2
(45) Date of Patent: Nov. 12, 2019

(54) SHOCK TUBE AND CELL ELECTROPORATION DEVICE WITH THE SHOCK TUBE

(71) Applicant: Jian Chen, Taizhou (CN)

(72) Inventor: Jian Chen, Taizhou (CN)

( * ) Notice: Subject to any disclaimer, the term of this patent is extended or adjusted under 35 U.S.C. 154(b) by 112 days.

(21) Appl. No.: 15/532,182

(22) PCT Filed: Dec. 2, 2015

(86) PCT No.: PCT/IB2015/059297
§ 371 (c)(1),
(2) Date: Jun. 1, 2017

(87) PCT Pub. No.: WO2016/088062
PCT Pub. Date: Jun. 9, 2016

(65) Prior Publication Data
US 2017/0335269 A1    Nov. 23, 2017

(30) Foreign Application Priority Data

Dec. 2, 2014   (CN) .......................... 2014 1 0722470
Dec. 1, 2015   (CN) ..................... 2015 2 0981250 U
Dec. 1, 2015   (CN) ..................... 2015 2 0981477 U

(51) Int. Cl.
*C12M 1/42*     (2006.01)
*C12M 1/24*     (2006.01)

(52) U.S. Cl.
CPC .............. *C12M 35/02* (2013.01); *C12M 1/24* (2013.01); *C12M 1/42* (2013.01); *C12M 23/08* (2013.01)

(58) Field of Classification Search
CPC ........ C12M 1/24; C12M 35/02; C12M 23/08; C12M 1/42
See application file for complete search history.

(56) References Cited

U.S. PATENT DOCUMENTS

2011/0253254 A1   10/2011   DeGruson et al.
2013/0052711 A1   2/2013    Chen

FOREIGN PATENT DOCUMENTS

| CN | 1965079 B | 12/2012 |
| CN | 203382763 U | 1/2014 |
| CN | 103865794 A | 6/2014 |
| CN | 104403943 A | 3/2015 |
| CN | 204311066 U | 5/2015 |
| KR | 10-2014-0112042 | 7/2014 |

OTHER PUBLICATIONS

International Search Report of PCT/IB2015/059297.

*Primary Examiner* — Gautam Prakash
(74) *Attorney, Agent, or Firm* — Minder Law Group; Willy H. Wong

(57) ABSTRACT

The shock tube comprises a tube, a first electrode, a second electrode and a stopple, wherein the tube is internally provided with a cavity for accommodating a target liquid sample. The first electrode is arranged at one end of the tube. The second electrode is arranged in the stopple, and the outer end of the second electrode can be electrically connected with the exterior via an opening of the stopple. The stopple is internally provided with an elastic piece connected with the second electrode. The outer side of the elastic piece is connected with the stopple, and the inner side of the elastic piece is connected with the second electrode. The invention further provides a cell electroporation device where the shock tube can be placed.

14 Claims, 20 Drawing Sheets

SHOCK TUBE AND CELL ELECTROPORATION DEVICE WITH THE SHOCK TUBE

RELATED APPLICATIONS

This application is a national stage entry of International Application No. PCT/IB2015/059297, filed Dec. 2, 2015, and claims benefit of Chinese Patent Application No. CN201410722470.9, filed Dec. 2, 2014; Chinese Patent Application No. CN201520981250.8, filed Dec. 1, 2015; and Chinese Patent Application No. CN201520981477.2, filed Dec. 1, 2015.

The above applications and all patents, patent applications, articles, books, specifications, other publications, documents, and things referenced herein are hereby incorporated herein in their entirety for all purposes. To the extent of any inconsistency or conflict in the definition or use of a term between any of the incorporated publications, documents, or things and the text of the present document, the definition or use of the term in the present document shall prevail.

BACKGROUND OF THE INVENTION

Field of Invention

The present invention belongs to the technical field of biomedical instruments and equipment, and in particular to a shock tube and cell electroporation device with the shock tube.

Related Art

Cell electroporation (also known as cell electrotransfection or cell electropermeabilization) is the technology of using electrical pulses to introduce macromolecules (which cannot penetrate the cell membrane) into cells. Electroporation is a method widely used and strongly recommended in cell experiments and gene therapy. When applying a strong electric field, a cell membrane is temporarily turned into permeable nature and may be penetrable by some foreign materials such as macromolecules. Cell membrane electroporation effect depends on various parameters of the electric field, such as pulse type, pulse voltage, pulse duration, number of pulses, and other experimental conditions.

Currently, the devices used for cell electroporation are mainly cell electroporator, cuvette etc. China's patent No. CN 1965079B discloses an electroporation device having an elongated hollow member. The electroporation device includes an elongated hollow member in order to provide a uniform electric field in the electroporation process, including in particular the implementation of electroporation by applying an electric pulse on the two ends of a long hollow member with a pair of electrodes after the hollow member is filled with cells and liquid sample of materials to be injected into cells.

The applicant had applied for US patent for an article entitled "Methods and devices for electroporation" (application number: US 2013/0052711 A1). The patent describes a sample container, herein referred to as shock tube. A shock tube is equivalent to the sample container in aforementioned U.S. patent application. Its function is to fill the tube with cells and liquid sample of materials to be injected into cells. Upper and lower ends of the shock tube are provided with an upper and lower electrode respectively; connection of the upper and lower electrodes to a cell electroporation device forms an electric field within the shock tube, thereby enabling injection of extracellular materials into the cells. After the shock tube is filled with liquid sample, the sample shape is fixed, and the liquid surface will not curve between the electrodes as occurred in a traditional open type cuvette. By eliminating the curved liquid surface, electric field inside the liquid becomes more uniform, and electroporation efficiency can be improved. After the liquid sample is loaded into the shock tube and prior to electroporation, it is necessary to prevent the formation of air bubbles by residual air which will affect electric current distribution. In the patent, the applicant has designed an annular groove on the tube wall of shock tube which is interconnected with the cavity of shock tube. Experimenters may inject liquid samples into shock tube cavity continuously until after the liquid surface is bulged out of the shock tube cavity. The upper electrode covers onto the bulged liquid surface until the upper edge of shock tube cavity is being pressed, thus forming a seal to the liquid inside the cavity. A small amount of spilled liquid will flow to the annular groove. This design can generally eliminate the presence of residual air in the shock tube which will affect the experiment. However, after numerous experiments, the applicant has found that the above-mentioned patent has relatively high requirement on manufacturing precision of the shock tube, and the requirement on the operation precision is relatively high too. If the manufacturing is not precise enough, it may easily lead to a bad sealing effect between the electrode and the upper edge of the cavity. Uptilting of the electrode may occur after being covered on the cavity, causing it to be separated again from the upper edge of cavity, thereby allowing ambient air to enter the cavity again. In addition, if used improperly by the operator, air bubbles may also be formed easily by residual air, which will affect the efficiency of cell electroporation. The requirement on reliability of instruments and equipment is very high in scientific research and experiments. Therefore, it is necessary to have some additional design to improve the reliability of operation.

SUMMARY OF THE INVENTION

In consideration of the above-mentioned problems of the prior art, one embodiment of the present invention provides a shock tube. The technical problems to be solved by one embodiment of the present invention are:

How to improve the sealing performance between the second electrode and end surface of the opening to prevent ambient air from entering the cavity;

How to ensure sealing performance of the shock tube and at the same time improve the stability of connection between the second electrode and stopple;

How to reduce the phenomenon of high voltage arc generated in the air outside the shock tube between two electrodes.

One embodiment of the present invention is directed to the aforementioned problems and provides a cell electroporation device with a shock tube. The technical problem to be solved is: how to improve the performance of electroporation of the cell electroporation device.

One objective of the shock tube of one embodiment of the present invention may be achieved by the following technical solution:

A shock tube, wherein the shock tube comprises a tube, a first electrode, a second electrode and a stopple. The tube is internally provided with a cavity for accommodating a target liquid sample, characterized in that, the first electrode is arranged at one end of the tube, and the other end of the tube is provided with an opening interconnected with the cavity. The working part of the first electrode is interconnected with the cavity. The edge of the opening has an annular end surface. The second electrode is arranged in the stopple, and the outer end of the second electrode can be electrically connected with the exterior via an opening of the stopple. The inner end surface of the second electrode can be well-matched with the annular end surface of the edge of opening. The second electrode and the stopple have an elastic connection in between. The periphery of the opening has a positioning structure which is capable of fixing the stopple at the end of tube and rendering the second electrode under elastic stress.

Its working principle is as follows: During operation, one embodiment of the shock tube can be filled up into the cavity with a liquid sample comprising cells and materials to be injected into the cells, forming a bulged liquid surface, then the stopple is secured to the end of tube via a positioning structure to generate a compressive deformation to the elastic piece between the stopple and the second electrode, while the second electrode is pressed against the end surface of the opening, the first electrode and second electrode are interconnected with the liquid in the cavity. Then the first electrode and second electrode are connected with the pulse power supply. Electrification produces an electric field within the shock tube, causing the cell membranes to possess certain permeability, so that the target material in the liquid sample can enter the cells. When the stopple is fixed to the end portion of the tube, a compressive deformation is generated in the elastic piece, to avoid the formation of gaps between the second electrode and the opening, improving the sealing performance between the second electrode and the end surface of the opening, thereby preventing air from entering the liquid sample in the cavity. In addition, when the stopple becomes slightly uptilted, the elastic piece can also make certain deformation recovery, to ensure the second electrode to remain closely abutting with the end surface of opening edge, so that still no air bubble will be generated in liquid sample in the cavity when there is some operation deviation during sample loading by the experimenter. In summary, the shock tube can effectively improve sealing performance between the second electrode and the opening, thus inhibiting ambient air from entering the cavity when loading liquid sample.

The positioning structure of one embodiment of the present application directly provides stable support and positioning to the outer end portion of elastic piece, so that the elastic piece remains in a stable compressed state between the stopple and second electrode, enabling the elastic piece to apply a stable elastic force to the second electrode, thus producing a more close and stable matching between the second electrode and end surface of the opening of tube, thereby enhancing the sealing effect of the second electrode and end surface of the opening of tube. The positioning structure and elastic piece are inseparable in jointly solving the technical problem of "how to enhance the sealing stability between the second electrode and the tube".

It is worthwhile to note that, one embodiment of the tube and the stopple in the present application are made of an insulating material. The first electrode and second electrode are made of an electrically conductive material, which is a part of the prior art, and the specific material being used is not the subject of this Specification. In addition, the first electrode may either be directly fixed to the tube, or may be installed inside a stopple, as with the second electrode, before being used to seal the cavity of tube.

In one embodiment of the shock tube, the stopple comprises the pipe having a first through-hole. The second electrode is disposed in the first through-hole. The second electrode comprises a rod and a cap. One end of the rod is fixedly connected with the cap. The other end of the rod can be electrically connected with the exterior via an opening of the stopple. The elastic piece is socket-connected on the outer side surface of rod. The outer end of the stopple has a retaining edge radially extended inward along first through-hole. The outer end surface of the elastic piece abuts against the retaining edge, and the inner end surface of the elastic piece abuts against the cap. The elastic piece is made of rubber and plastic materials. Rubber and plastic materials include plastics, rubber, silicone and the like. When the stopple is fixed to the end portion of the tube, the second electrode is well-matched with end surface of the edge of opening of tube cavity. The elastic piece generates a compressive deformation to improve sealing effect of the second electrode with end surface of the edge of opening. The rod of second electrode can be electrically connected with the exterior via an opening of the retaining edge of the stopple. The rod of second electrode may extend to the exterior of the stopple to allow electrical connection with the second electrode. The rod may also not extend to the exterior of the stopple. The external electrical connection contacts may be inserted into the stopple via the opening of the stopple to connect to the second electrode. The elastic piece may be fabricated generally in a ring shape and may also be a partial ring shape or even other shapes, as long as it is resilient and capable of being plugged with the second electrode. In the shock tube, the elastic piece may be a separate elastic piece mounted in first through-hole with an interference fit method, or mounted in first through-hole by bonding or other methods and connected with the stopple. The elastic piece may be socket-connected on the rod of the second electrode with an interference fit or bonding method.

In one embodiment of the shock tube, a first retaining shoulder is provided between the elastic piece and the cap. The first retaining shoulder is located between the elastic piece and the cap. The size or the spatial dimension of the first retaining shoulder is larger than the diameter of rod and smaller than the diameter of cap. The first retaining shoulder separates the cap from the elastic piece, causing the cap, in compressing the elastic piece, may only apply stress through the first retaining shoulder. The diameter or size of first retaining shoulder is smaller than the cap and elastic piece, thereby producing relatively greater pressure on a small contact area, prompting easy deformation and displacement of elastic piece. When the stopple is fixed in the positioning structure, the second electrode is well-matched with end surface of the opening. The elastic piece is in compressed state under pressure from the second electrode. Pressure is generated by this compressive deformation and exerted to end surface of opening at end of tube to improve sealing performance, and when the stopple is slightly uptilted, a certain deformation recovery will be generated to continue pressing the second electrode against the end surface of opening at end of tube.

In one embodiment of the shock tube, the first retaining shoulder may be a separate component, such as a separate ring shape retaining shoulder of size smaller than the elastic piece and the cap. The first retaining shoulder is socket-fitted on the rod between the elastic piece and the cap, and its material may be an insulator or non-insulator.

In one embodiment of the shock tube, as a second case, the first retaining shoulder is fixedly arranged on the cap, or the first retaining shoulder forms an integral body with the cap and rod. The inner end surface of the elastic piece abuts against the end surface of the first retaining shoulder. When the rod is plugged the elastic piece, the cap is separated from the elastic piece, and the cap and the elastic piece mutually exert stresses through the first retaining shoulder.

In one embodiment of the shock tube, as a third case, the first retaining shoulder is fixedly arranged on the elastic piece, or the first retaining shoulder forms an integral body with the elastic piece. The first retaining shoulder abuts against the cap.

In one embodiment of the shock tube, as a solution for an alternative elastic piece, the connection method of elastic piece with the stopple is a direct connection. The stopple comprises the pipe having a first through-hole. The second electrode is disposed in the first through-hole. The second electrode comprises a rod and a cap. One end of the rod is fixedly connected with the cap. The other end of the rod can be electrically connected with the exterior via an opening of the stopple. The elastic piece is a resilient retaining edge elastic piece extended inward along first through-hole on inner wall of the first through-hole. The retaining edge elastic piece abuts against the outer side surface of the rod. The material of retaining edge elastic piece is the same as the stopple. Its outer side forms an integral body with inner wall of the stopple body, and an opening is formed in its center. The rod of second electrode is plugged to the opening of retaining edge elastic piece by interference fit or bonding method etc. Due to precision requirement of the shock tube body, it is generally necessary to be manufactured with certain strength to prevent deformation. As an elastic piece, the retaining edge elastic piece, which forms an integral body with the stopple, may use the strength reduction design thereby to achieve flexibility, such as designing a thinner portion than the other portions, so that it is more prone to generate compressed deformation. The retaining edge elastic piece may generally be made into a ring shape, or it may not be in ring shape, as long as it is flexible and can be plugged with the second electrode.

In one embodiment of the shock tube, as a first case, a second retaining shoulder is provided between the retaining edge elastic piece and the cap. The size or spatial dimension of the second retaining shoulder is larger than the diameter of rod and smaller than the diameter of cap. The second retaining shoulder may be a separate retaining ring.

In one embodiment of the shock tube, as a second case, the second retaining shoulder is fixedly arranged on the cap or the second retaining shoulder forms an integral body with the cap and rod. The inner end surface of the retaining edge elastic piece abuts against the end surface of the second retaining shoulder.

In one embodiment of the shock tube, as a third case, the second retaining shoulder is fixedly arranged on the retaining edge elastic piece or the second retaining shoulder forms an integral body with the retaining edge elastic piece. The second retaining shoulder abuts against the cap.

In one embodiment of the shock tube, as a solution for third type of elastic piece, the elastic piece is a compression spring. The stopple comprises a pipe having a first through-hole. The second electrode is disposed in the first through-hole. The second electrode comprises a rod and a cap. One end of the rod is fixedly connected with the cap. The other end of the rod can be electrically connected with the exterior via an opening of the stopple. The compression spring is socket-connected on the outer side surface of the rod. The outer end of the stopple has a retaining edge radially extended inward along the first through-hole. The outer end surface of the compression spring abuts against the retaining edge, and the inner end surface of the compression spring abuts against the cap. When the stopple is fixed to the end part of tube, the compression spring can generate a deformation compression to improve the sealing performance between the second electrode and the end part of tube at the edge of opening.

In one embodiment of the shock tube, the positioning structure comprises a connecting tube which forms an integral body with the end part of the tube. The connecting tube is provided with a chamber for the stopple to plugin. The chamber wall of the chamber has a first rib. The outer side surface of the stopple has a second rib which can snap-connect with first rib. The first rib and second rib may be of a complete annular shape or discontinuous annular shape or even non-annular shape. A snap-connection effect can be achieved in all cases. The protrusions of first rib and second rib may not be obvious. A stopple of size slightly larger than the internal size of the connecting tube is used to insert into the tube portion, to achieve the purpose of positioning by interference fit method. The stopple is snap-connected with the connecting tube, making both connection and separation of the two very easy, to enhance the convenience in liquid injection and pipetting after the completion of electroporation. Of course the threaded connection method may also be used. While using threaded connection, the stopple can be fixed to the connecting tube by rotating it.

In one embodiment of the shock tube, the positioning structure comprises a first strike disposed on the stopple. The tube is provided with a first latch which can snap-connect with the first strike.

In one embodiment of the shock tube, the end surface of the edge of opening is provided with an annular groove. During operation, the shock tube can be filled up into the cavity with a liquid sample until the liquid sample has formed a bulged surface on the opening, and then the second electrode is in contact with the bulged liquid surface, and presses downward to seal the opening to ensure that no residual air is inside the cavity. The excess liquid needed in forming the bulged surface will overflow into the annular groove, without affecting the cell electroporation process in liquid sample in the cavity.

In one embodiment of the shock tube, the stopple and the tube is connected by a flexible link. The two ends of the flexible link are connected with the stopple and tube respectively, so that the stopple is connected with the tube but also able to swing in relative to the tube, avoid accidental loss of the stopple. The plastic material of the flexible link is fabricated relatively thin so as to achieve the flexibility of large angle bending.

In one embodiment of the shock tube, outer side of the elastic piece and the stopple are well-matched and form a seal. Inner side of the elastic piece and outer side surface of the second electrode are well-matched and form a seal.

In one embodiment of the shock tube, the cavity of tube is provided with an ion conductive layer. The bottom layer surface of the ion conductive layer is in contact with a first electrode. The upper layer surface of the ion conductive layer is capable of contacting with the target liquid sample. This design separates the cell sample from direct contact with the first electrode, so as to avoid direct damage to the cell sample by electrochemical reaction near the first electrode. The ion conductive layer contains components of a soluble salt as the ion source, and may contain gel substance such as agarose, agar, polyacrylamide, colloidal protein etc. to form a gel or semi-solid state, or may contain porous solids infiltratable by the salt solution to form a state capable of ion-conduction state.

A further objective of the shock tube of one embodiment of the present invention may be achieved by the following technical solution:

A shock tube, wherein the shock tube comprises a tube and a stopple. The tube is internally provided with a cavity for accommodating a target liquid sample. The first electrode interconnected with the cavity is arranged at one end or middle part of the tube, and the other end of the tube is provided with an opening interconnected with the cavity. The second electrode is arranged in the stopple, and the second electrode comprises a rod and a cap. One end surface of the cap can be well-matched with the annular end surface of the edge of opening. An elastic connection is provided between the second electrode and the stopple, characterized in that, the rod is inserted into the stopple and slidably connected to the stopple. A limiting structure is further provided between the second electrode and the stopple to prevent separation of the rod from the stopple.

Its working principle is as follows: During operation, one embodiment of the shock tube can be filled up into the cavity from opening of tube with a liquid sample comprising cells and materials to be injected into the cells, then the stopple is secured to the end of tube. Outer end surface of the cap of second electrode is well-matched with the annular end surface at the edge of tube opening. One end of the first electrode and second electrode are interconnected with the liquid in the cavity, and the other ends of first electrode and second electrode can be electrically connected with the exterior, so the first electrode and second electrode are connected with the pulse power supply. Electrification produces an electric field within the cavity of shock tube, causing the cell membranes to possess certain permeability, so that the target material in the liquid sample can enter the cells. In the present technical solution, when the stopple is fixed to the end portion of the tube, the elastic piece is positioned between the stopple and the cap of second electrode, and capable of forming a seal between the cap and the stopple. The rod of second electrode is plugged to the stopple and slidably connected to the stopple, and capable of effectively preventing the second electrode from falling off the stopple via a limiting structure.

In one embodiment of the shock tube, the limiting structure comprises a rim extended from outer end of the rod along the radial direction of the rod. Radial size of the rim is slightly larger than the diameter of the opening of the stopple. The rim is capable of pressing the stopple, under external force, to generate a deformation and passes out of the opening. After the stopple is deformed under external compression, the rim can pass smoothly through the stopple. After the stopple has recovered from the deformation, the rim can maintain the limitation with the stopple, effectively preventing the second electrode from falling off.

In one embodiment of the shock tube, opening part of the stopple has an abutment surface abutting against the rim. After the stopple is deformed under external compression, the rim can pass smoothly through the stopple and maintain the limitation by matching with the abutment surface to prevent the second electrode from falling off.

In one embodiment of the shock tube, the rim is cone shape. Outer side surface of the rim has a first guiding surface obliquely extended towards outer side surface from end surface of rim. Through the guiding effect of first guiding surface, it is possible to facilitate the installation and placement of the second electrode.

In one embodiment of the shock tube, the stopple comprises a pipe having a first through-hole. The rod is inserted into the first through-hole. The limiting structure comprises an annular bulge on inner side wall of pipe. The cap is disk shape, and outer diameter of the cap is larger than inner diameter of the annular bulge. The cap can pass through the annular bulge in such a way that the outer end surface of cap is above the upper side surface of the annular bulge. As a solution of alternative limiting structure, after the annular bulge on pipe is deformed under external compression, the cap can pass smoothly through the inner hole of annular bulge. After the annular bulge has recovered from the deformation, the outer end surface of cap abuts against the upper side surface of annular bulge and maintains the limitation, effectively preventing the second electrode from falling off.

In one embodiment of the shock tube, the height of pipe of the stopple is greater than height of the elastic piece. So the elastic piece is positioned within the pipe, and the cap of second electrode is also positioned within the pipe. A limiting effect is applied to second electrode and elastic piece through the pipe, and further, also enables the cap of second electrode and inner wall of pipe to form a seal, so as to improve sealing performance.

In one embodiment of the shock tube, the pipe is provided with a tubular mounting seat. The second electrode is slidably connected on the mounting seat. The elastic piece is socket-fitted on the mounting seat. The height of the elastic piece is greater than the height of mounting seat. When the stopple is fixed to the end portion of tube, the elastic piece generates a compressive deformation, causing upper end surface of elastic piece abuts against the stopple and lower end surface of elastic piece abuts against upper end surface of the cap. The elastic piece is positioned between the pipe of the stopple and the mounting seat, and both ends of the elastic piece abut against the stopple and second electrode respectively. The elastic piece generates compressive deformation, so that the elastic piece forms a seal with the stopple and second electrode, preventing occurrence of gaps between the second electrode and the opening of tube, and inhibiting air from entering the liquid sample in cavity. Further, when the stopple becomes slightly uptilted, the elastic piece can also make certain deformation recovery, to ensure the second electrode to remain closely abutting with the end surface of opening edge, so that still no air bubble will be generated in liquid sample in the cavity when there is some operational deviation during sample loading by the experimenter. In summary, the technical solution can effectively improve sealing performance between second electrode and opening, thus inhibiting ambient air from entering the cavity when loading liquid sample.

Since the elastic piece is positioned between the pipe of the stopple and mounting seat, and its upper and lower ends abut against the stopple and second electrode respectively, the elastic piece will not fall off. Meanwhile the elastic piece may perform limitation to the cap of second electrode to prevent excessive movement of the second electrode.

In one embodiment of the present technical solution, the tube and stopple are made of an insulating material. The first electrode and second electrode are made of an electrically conductive material, which is a part of the prior art, and the specific material being used is not the subject of this Specification. In addition, the first electrode may either be directly fixed to the tube, or may be installed inside a stopple, as with the second electrode, before being used to seal the cavity of tube.

In one embodiment of the shock tube, the inner side wall of the mounting seat is provided with a third guiding surface obliquely extended to inner side wall from end surface of the mounting seat. Through the guiding effect of third guiding surface, it is possible to facilitate the installation and placement of the second electrode.

In one embodiment of the shock tube, there is a gap between outer side surface of the elastic piece and inner side wall of the pipe of the stopple. The retaining of this gap can provide a certain amount of space for deformation of elastic piece, so that the automatic adjustment of gap sealing between the stopple and second electrode is achieved by using the recovery force of elastic piece.

In one embodiment of the shock tube, the stopple comprises a pipe having a first through-hole. The rod is inserted into the first through-hole. The pipe is provided with a tubular mounting seat inside. The second electrode is slidably connected on the mounting seat. The elastic piece is the resilient part at lower end of the mounting seat. The joint of the rod and cap is provided with a slope abutting against the end surface of the elastic piece. The rod has a slope for inserting into mounting seat. After the slope is inserted into the mounting seat, the elastic piece on the mounting seat is elastically deformed to improve sealing performance.

In one embodiment of the shock tube, the periphery of the opening has a positioning structure which is capable of fixing the stopple at the end of tube and generating a compressive deformation to the elastic piece. Through the positioning structure, the elastic piece is deformed to further improve the sealing performance, while effectively preventing the stopple from falling off the end of tube.

In one embodiment of the shock tube, the positioning structure comprises a connecting tube which forms an integral body with the end part of the tube. The connecting tube is provided with a chamber for the stopple to plugin. The chamber wall of the chamber has a first rib. The outer side surface of the stopple has a second rib which can snap-connect with the first rib. The first rib and second rib may be of a complete annular shape or discontinuous annular shape or even non-annular shape. A snap-connection effect can be achieved in all cases. The protrusions of first rib and second rib may not be obvious. A stopple of size slightly larger than the internal size of connecting tube is used to insert into the tube portion, to achieve the purpose of positioning by interference fit method. The stopple is snap-connected with the connecting tube, making both connection and separation of the two very easy, to improve the convenience in liquid injection and pipetting after the completion of electroporation. Of course the threaded connection method may also be used. While using threaded connection, the stopple can be fixed to the connecting tube by rotating it.

In one embodiment of the shock tube, as an alternative solution, the positioning structure comprises a first strike disposed on the stopple. The tube is provided with a first latch which can snap-connect with the first strike.

In one embodiment of the shock tube, the end surface at edge of the opening has an annular groove. The stopple and the tube are connected by a flexible link. The two ends of the flexible link are connected with the stopple and tube respectively, so that the stopple is connected with the tube but also able to swing in relative to the tube, to avoid accidental loss of the stopple. The plastic material of the flexible link is fabricated with a relatively thin. It can achieve the flexibility of large angle bending. This will not interfere with the removal of the stopple from the tube, and it can also prevent loss of the stopple from falling off. It is very convenient to use.

A further objective of shock tube of one embodiment of the present invention may be achieved by the following technical solution:

A shock tube, wherein the shock tube comprises a stopple and an integrally fabricated tube. The tube is internally provided with a cavity for accommodating a target liquid sample. One end of the tube is provided with an opening interconnected with the cavity. A second electrode is arranged in the stopple, and the outer end of the second electrode can be electrically connected with the exterior via an opening of the stopple. The inner end surface of the second electrode can be well-matched with the annular end surface of the edge of opening, characterized in that, a first electrode interconnected with cavity is arranged at middle of the tube. The first electrode forms a seal with the tube. The part of tube below first electrode is the extension segment, which is capable of preventing the first electrode and second electrode from generating a high voltage arc on the outer side of the tube.

Its working principle is as follows: During operation, one embodiment of the shock tube can be filled up into the cavity from opening of tube with a liquid sample comprising cells and materials to be injected into the cells, then the stopple is secured to the end of tube making inner end surface of second electrode well-matched with the annular end surface at the edge of tube opening. Both first electrode and second electrode are interconnected with the liquid in the cavity. The electrode terminal may extend through the extension segment of the tube and electrically connected with the first electrode. The outer end of the second electrode can be electrically connected with the exterior via an opening of the stopple. The outer ends of the first electrode and second electrode are connected with the pulse power supply. Electrification produces an electric field within the cavity of shock tube, causing the cell membranes to possess certain permeability, so that the target material in the liquid sample can enter the cells. In the present technical solution, the part of tube below first electrode is the extension segment, which is capable of preventing the first electrode and second electrode from generating a high voltage arc on the outer side of the tube. The extension segment has good insulation performance, and generally does not breakdown under pulse voltage. The first electrode and second electrode will have to bypass the extension segment to produce a high voltage outside the tube. The air breakdown distance between the first electrode and second electrode is extended greatly by the addition of extension segment. Even if a very high voltage is applied, it can effectively prevent the breakdown between first electrode and second electrode in the ambient air of tube, thereby ensuring the current to achieve electroporation to the target liquid sample in cavity.

In addition, one embodiment of the extension segment is serving as a handle too, for convenient handling of the shock tube by users.

In one embodiment of the present technical solution, the tube and stopple are made of an insulating material. The first electrode and second electrode are made of an electrically conductive material, which is a part of the prior art, and the specific material being used is not the subject of this Specification. In addition, the first electrode may either be directly fixed to the tube, or may be installed inside a stopple, as with the second electrode, before being used to seal the cavity of tube.

In one embodiment of the shock tube, the length of the extension segment is generally between 1 mm and 40 mm, based on needs. Preferably, the length of the extension segment may be between 2 mm and 30 mm. More commonly, it is between 5 mm and 20 mm. When the length of extension segment is greater than the length of cavity, the air breakdown path distance between the first electrode and second electrode outside the tube is at least three times the length of cavity. Hence the first electrode and second electrode are almost impossible to produce a high voltage arc outside the tube.

In one embodiment of the shock tube, the tube is made of a plastic material. The wall thickness of tube in extension segment is smaller than the wall thickness of tube in the cavity. The wall thickness of tube in the cavity is relatively larger to prevent the high voltage breakdown between the first electrode and the second electrode. In the meantime, the wall thickness of tube in extension segment is less than the wall thickness of tube in the cavity to facilitate the insertion of first electrode from the extension segment into the tube and installed in the middle of the tube, and also facilitates the insertion of electrode terminal into the extension segment of tube to have electrical connection with the first electrode.

In one embodiment of the shock tube, the interior diameter of the tube in extension segment is greater than the interior diameter of the tube in the cavity and forms a step in the tube. The first electrode has a flange and a peg located at upper side of flange. The end surface of the flange is in contact with the step. The peg is snap-connected in the tube hole of the cavity. The step and flange coordinate with each other to play a role in positioning limitation to improve ease of installation while ensuring sealing performance and to prevent leakage of target liquid sample.

In one embodiment of the shock tube, a contact part is disposed at lower side of flange of the first electrode. The diameter of the contact part is smaller than diameter of flange, and there is a gap between the contact part and tube wall of extension segment of the tube. The contact part can also facilitate the handling, placement and installation of the second electrode.

In one embodiment of the shock tube, the length of the contact part is usually short, to prevent too close a distance from first electrode to lower end of extension segment, which may, bypassing the extension segment, induce voltage arc.

In one embodiment of the shock tube, the stopple is internally provided with an elastic piece connected with the second electrode. The outer side of the elastic piece is connected with the stopple, and the inner side of the elastic piece is connected with the second electrode. When the stopple is fixed to the end portion of the tube, the elastic piece generates a compressive deformation, so that the elastic piece forms a seal with the stopple and second electrode, preventing occurrence of gaps between the second electrode and the opening of tube, and inhibiting air from entering the liquid sample in cavity. Further, when the stopple becomes slightly uptilted, the elastic piece can also make certain deformation recovery, to ensure the second electrode to remain closely abutting against the end surface of opening edge, so that still no air bubble will be generated in liquid sample in the cavity when there is some operation deviation during sample loading by the experimenter. In summary, the present technical solution can effectively improve sealing performance between second electrode and opening, thereby inhibiting ambient air from entering the cavity when loading liquid sample.

In one embodiment of the shock tube, the stopple comprises the pipe having a first through-hole. The second electrode is disposed in the first through-hole. The second electrode comprises a rod and a cap. One end of the rod is fixedly connected with the cap. The other end of the rod can be electrically connected with the exterior via an opening of the stopple. The elastic piece is socket-connected on the outer side surface of rod. The outer end of the stopple has a retaining edge radially extended inward along first through-hole. The outer end surface of the elastic piece abuts against the retaining edge, and the inner end surface of the elastic piece abuts against the cap. The elastic piece is made of rubber and plastic materials. Rubber and plastic materials include plastics, rubber, silicone and the like. When the stopple is fixed to the end portion of the tube, the second electrode is well-matched with end surface of the edge of opening of tube cavity. The elastic piece generates a compressive deformation to improve sealing effect of the second electrode with end surface of the edge of opening. The rod of second electrode can be electrically connected with the exterior via an opening of the stopple retaining edge. The rod of second electrode may extend to the exterior of the stopple to allow electrical connection with the second electrode. Of course the rod may also not extend to the exterior of the stopple, and instead the external electrical connection contacts is inserted into the stopple via stopple opening to be connected to the second electrode. The elastic piece may be formed generally into ring shape, and may be a partial ring shape or even other shapes, as long as it is resilient and capable of being plugged with the second electrode. The elastic piece may be a separate elastic piece mounted in first through-hole with an interference fit method, or mounted in first through-hole by bonding or other methods and connected with the stopple.

In one embodiment of the shock tube, as an alternative solution, the stopple comprises a pipe having a first through-hole and a tubular mounting seat located in the pipe. The second electrode is slidably connected on the mounting seat and an annular elastic piece is socket-fitted outside the mounting seat. The height of elastic piece is greater than the height of mounting seat. The second electrode comprises a rod and a cap. Inner end of the rod is fixedly connected with the cap. The outer end of the rod can be electrically connected with the exterior via an opening of the stopple. The outer end of the rod has a rim radially extended along the rod. The size of the rim is slightly larger than the opening of the stopple. Opening part of the stopple has an abutment surface abutting against the rim. The elastic piece is positioned between the pipe and the mounting seat. When the stopple is fixed to the end portion of the tube, a compressive deformation is generated by the elastic piece, causing the outer end surface of the elastic piece abutting against the stopple, and the inner end surface of elastic piece abuts against the cap. The elastic piece is positioned between the pipe of the stopple and mounting seat, and will not fall off. In addition, as long as the stopple and second electrode abut against the two ends of elastic piece respectively, a seal is achieved. While installation is facilitated, sealing performance is also ensured.

In one embodiment of the shock tube, the elastic piece is socket-fitted on outer side surface of the mounting seat, and inner side surface of the elastic piece is in contact with outer side surface of the mounting seat. The inner side surface and upper end surface of elastic piece is in contact and abuts against the stopple, forming a multi-surface sealing connection, which, in addition to the sealing connection formed between inner end surface of elastic piece and the second electrode, further improve the sealing performance.

In one embodiment of the above technical solutions, the first electrode is multi-segmentally cylindrical or conical in shape. The outer side wall at upper end of first electrode has an annular band along the circumference of the first electrode. The annular band forms a well-matched seal with the inner wall of the cavity. The outer side surface of the flange and the tube wall of extension segment may be allowed some gaps for easy installation. The formation of seal by local annular band and inner wall of the cavity can facilitate installation and reducing resistance when the first electrode is placed. The length of extension segment in the present technical solution is ⅓ ~⅔ of the total length of tube.

The objectives of one embodiment of the cell electroporation device with the shock tube of present invention can be achieved by the following technical solutions:

A cell electroporation device with a shock tube, wherein the cell electroporation device comprises a housing. The housing is disposed with a fixing base. The fixing base is provided with a socket. Characterized in that, the cell electroporation device also comprises a shock tube which can be plugged in the socket. The shock tube comprises a tube, a first electrode, a second electrode and a stopple, wherein the tube is internally provided with a cavity for accommodating a target liquid sample. The first electrode is arranged at one end of the tube, and the other end of tube is provided with an opening interconnected with the cavity. The working part of the first electrode is interconnected with the cavity. The edge of the opening has an annular end surface. The second electrode is arranged in the stopple, and the outer end of the second electrode can be electrically connected with the exterior via an opening of the stopple. The inner end surface of the second electrode can be well-matched with the annular end surface of the edge of opening. The stopple is internally provided with an elastic piece connected with the second electrode. The outer side surface of the elastic piece is connected with the stopple, and the inner side of the elastic piece is connected with the second electrode. The periphery of opening has a positioning structure which is capable of fixing the stopple at the end portion of tube generating a compressive deformation to the elastic piece. The inner end of the socket has a first electrode terminal which can be electrically connected to the first electrode. The housing is provided with a cover for covering the outer end of socket. The cover is disposed with a second electrode terminal which can be electrically connected with the second electrode. The housing is also provided with a power module which is electrically connected to the first electrode terminal and second electrode terminal.

Its working principle is as follows: During operation, one embodiment of the cell electroporation device can be filled up into the tube cavity with a liquid sample and then covered with stopple. After the shock tube is placed in the socket, the cover is closed, so the first electrode terminal is electrically connected to the first electrode, and the second electrode terminal is electrically connected to the second electrode, and the pulse power is turned on to supply electricity, forming an electric field within the shock tube, enabling the injection of extracellular substances into the cells. Preferably, the shock tube is arranged vertically, and the two electrodes of shock tube are set in upper and lower positions respectively. The first electrode terminal and second electrode terminal are correspondingly disposed above and beneath the shock tube respectively.

Since one embodiment of the stopple is also provided with an elastic piece for enhancing the action force between the second electrode and the end surface of opening, thus inhibiting gaps to occur between the second electrode and the opening. In addition, when the stopple becomes slightly uptilted, the elastic piece can also make certain deformation recovery, to ensure the second electrode to remain closely abutting with the end portion of tube at end surface of opening, thus inhibiting ambient air from entering the cavity. Meanwhile, the internal generation of gas bubbles by electrochemical reaction in the shock tube during electroporation process can also be restrained. In summary, the shock tube of the cell electroporation device can effectively improve sealing performance between the second electrode and the end surface of opening, thus inhibiting ambient air from entering the cavity and forming air bubbles during the electroporation preparation process. Since air bubbles are basically non-conductive, the electric current can only flow through the gap between air bubbles, resulting in a strong electric current in the gaps of air bubbles, causing the cells to die easily. The electric current before and after the air bubbles (relative to the main current flow direction) is weak, causing difficulty in cell electroporation, thus affecting the electrotransfection. The shock tube device of present invention has reduced the influence of gas bubbles, which is generated by electrochemical reaction, on electric current during the electroporation process, thereby improving the electroporation performance of the cell electroporation device.

In one embodiment of the cell electroporation device with the shock tube, the fixing base comprises a seat and a clamping cylinder. The socket is disposed inside the clamping cylinder. A silo is provided in the seat. The clamping cylinder is inserted in the silo and both are detachable and interconnectable with each other. Since the clamping cylinder and silo are detachable and can be interconnected with each other, the clamping cylinder with corresponding size of socket diameter can be replaced, depending on different diameter size of the shock tube, thus increasing versatility of this cell electroporation device.

In one embodiment of the cell electroporation device with the shock tube, the clamping cylinder is made of a material with light transmittance greater than 50%.

In one embodiment of the cell electroporation device with the shock tube, the bottom of the clamping cylinder abuts with the bottom of the silo. The top end of clamping cylinder is provided with at least one handle. With handle provided in the design, assembly and disassembly of clamping cylinder is more convenient for the operator. To accommodate shorter shock tubes, a metal electrode extension piece can also be mounted at the bottom of the clamping cylinder. The bottom part of metal extension piece is in contact with first electrode terminal. Electrical connection is made through the metal extension piece between first electrode and first electrode terminal, when a shorter shock tube is inserted into the clamping cylinder, and the height deficiency of shock tube is compensated in this manner.

In one embodiment of the cell electroporation device with the shock tube, the seat contains also a hollow. The silo has a second through-hole at its bottom. The two ends of the second through-hole are connected with the socket and hollow respectively. The hollow is provided with a spring seat and a spring. The inner end of the spring is fixed on the spring seat, and the outer end of the spring is connected to the inner end of the first electrode terminal. The outer end of the first electrode terminal can pass through the second through-hole and inserts in the socket. After the spring seat and spring are provided in the design, when the socket opening is closed by the cover, the first electrode and second electrode can be connected to the first electrode terminal and second electrode terminal respectively. When the shock tube is pressed by the cover, the spring is compressed and a greater extra pressure is generated. This pressure is exerted through a second electrode to the opening of cavity, enhancing the sealing performance of second electrode and opening of cavity. During the cell electroporation process, due to the electrochemical reaction, the electrolysis process will produce some air or gas bubbles. When gas bubble pressure is generated between the second electrode and the opening of cavity, the pressure produced by the spring can be exerted to the cell sample to counter the gas bubble pressure. These electrochemical gas bubbles will be compressed and its influence to the distribution of electric current in the electroporation process will be reduced, thereby increasing cell electroporation effect. In general, the pressure requirement for common spring to provide electrical contact point pressure is not much, especially when the voltage is as high as several hundred volts to thousand volts or even higher. A low pressure such as a load of less than 1 N (Newton) is sufficient to provide proper electrical connection. Unlike a common spring for electrical contacts, the function of spring in the cell electroporation device of present invention is not only to provide pressure for electrical contacts, but also required to generate a greater additional pressure to counter electrolytic air bubble pressure. The higher pressure here generally refers to a stress over 1 N, or above 2 N, or higher than 4 N, or even higher after the spring is compressed. After the completion of cell electroporation, when the cover is opened, the shock tube may pop up partially from the socket under the action of spring, making it convenient to pick it up.

In one embodiment of the cell electroporation device with the shock tube, the cover is made of a material with light transmittance greater than 50%. The seat accessory is provided with a sensor for detecting the displacement change of shock tube. The housing is internally provided with a micro control unit electrically connected with the sensor. The housing is also provided with an indicator lamp. The indicator lamp is connected with the power module. Signals of the sensor can be transmitted to the micro control unit for controlling the indicator lamp. In addition to the function of indicating the connection status of shock tube, it can also serve the function of illumination. A brighter indicator lamp such as LED light can be used to illuminate the shock tube. The sensor can be a mechanical trigger switch. The switch will be triggered by its linkage bar when displacement of first electrode terminal occurs. The sensor can also be a photoelectric switch. The photoelectric switch will be triggered by an impacted optical path when displacement of first electrode terminal occurs. The sensor can also be a Hall switch etc., triggered when displacement of the shock tube or first electrode terminal occurs.

In one embodiment of the cell electroporation device with the shock tube, the indicator lamp can be mounted on housing near the shock tube socket, providing lights to illuminate the shock tube nearby. The indicator lamp can also be mounted on the fixing base. A transverse through-hole may be provided on the fixing base to install the indicator lamp. The clamping cylinder may be made of a transparent material. The indicator lamp on the fixing base may be used to illuminate the shock tube laterally through the clamping cylinder, achieving a clearer visual effect. Also, transparent clamping cylinders of different sizes can accommodate shock tubes of different sizes.

In one embodiment of the cell electroporation device with the shock tube, the housing is provided with a display screen. The housing is provided with a sampler. The micro control unit is connected with display screen and power module. The sampler is connected with shock tube and micro control unit respectively. Electrical signal collected by the sampler can be transmitted to a micro control unit and displays in the form of wave curves on the display screen. A power supply module can generate electric pulses required in cell electroporation. The housing is provided with a display screen for displaying instrumental and experimental information as well as displaying the experiment operation interface. The micro control unit in housing can control the power module and display screen. The micro control unit includes a programmable microcomputer and other microprocessors etc. The sampler can collect electrical signals in cell electroporation process, including voltage or current signals. The sampler includes resistors and other electronic components. Electrical signals are being processed via the micro control unit, and can be displayed in the form of wave curves on the display screen.

In one embodiment of the cell electroporation device with the shock tube, inner end of the cover is hinged to the housing. Outer end of the cover is provided with a second latch. The housing is also provided with a second strike which can snap-connect with the second latch. One end of cover is hinged to the housing, and the other end is snap-connected with the housing to facilitate the opening and closing of cover.

Compared with the prior art, one embodiment of the present invention has the following advantages:

1. When the stopple is fixed to the end portion of the tube, a compressive deformation is generated by the elastic piece, to avoid the formation of gaps between the second electrode and the opening, improving the sealing performance between the second electrode and the end surface of the opening, thereby preventing air from entering the liquid sample in the cavity. In addition, when the stopple becomes slightly uptilted, the elastic piece can also make certain deformation recovery, to ensure the second electrode to remain closely abutting with the end surface of opening edge, so that still no air bubble will be generated in liquid sample in the cavity when there is some operation deviation during sample loading by the experimenter. In summary, the shock tube can effectively improve sealing performance between the second electrode and the opening, thus inhibiting ambient air from entering the cavity when loading liquid sample.

2. The part of tube below first electrode is the extension segment, which is capable of preventing the first electrode and second electrode from generating a high voltage arc on the outer side of the tube. The extension segment has good insulation performance. The first electrode and second electrode will have to bypass the extension segment to produce a high voltage arc on the outer side of the tube. The air breakdown distance between the first electrode and second electrode is extended greatly by the provision of extension segment. Even if a very high voltage is applied, it can effectively prevent the breakdown between first electrode and second electrode in the ambient air on outer side of tube, thus ensuring the electric pulse to achieve electroporation to the target liquid sample in cavity.

3. The rod of second electrode is inserted into the stopple and slidably connected to the stopple, and capable of effectively preventing the second electrode from falling off the stopple via a limiting structure.

4. When the shock tube is pressed by the cover of cell electroporation device of the present invention, an extra pressure is generated. This pressure is exerted through a second electrode to the end of tube at the edge of opening, enhancing the sealing performance of second electrode and the edge of opening, enabling the compression of electrochemical air bubbles generated by electrochemical reaction in the solution to a certain extent during the cell electroporation process, thereby reducing its influence to the distribution of electric current in the electroporation process and increase the cell electroporation effect.

5. The cell electroporation device of present invention enables the experimenter to observe the state of shock tube, helping the experimenter to observe and control the progress of experiments.

6. The cell electroporation device of present invention can display the actual current or voltage waveform in cell electroporation process to facilitate the experimenter to observe and control the progress of experiments.

DETAILED DESCRIPTION OF THE INVENTION

Figure 1:
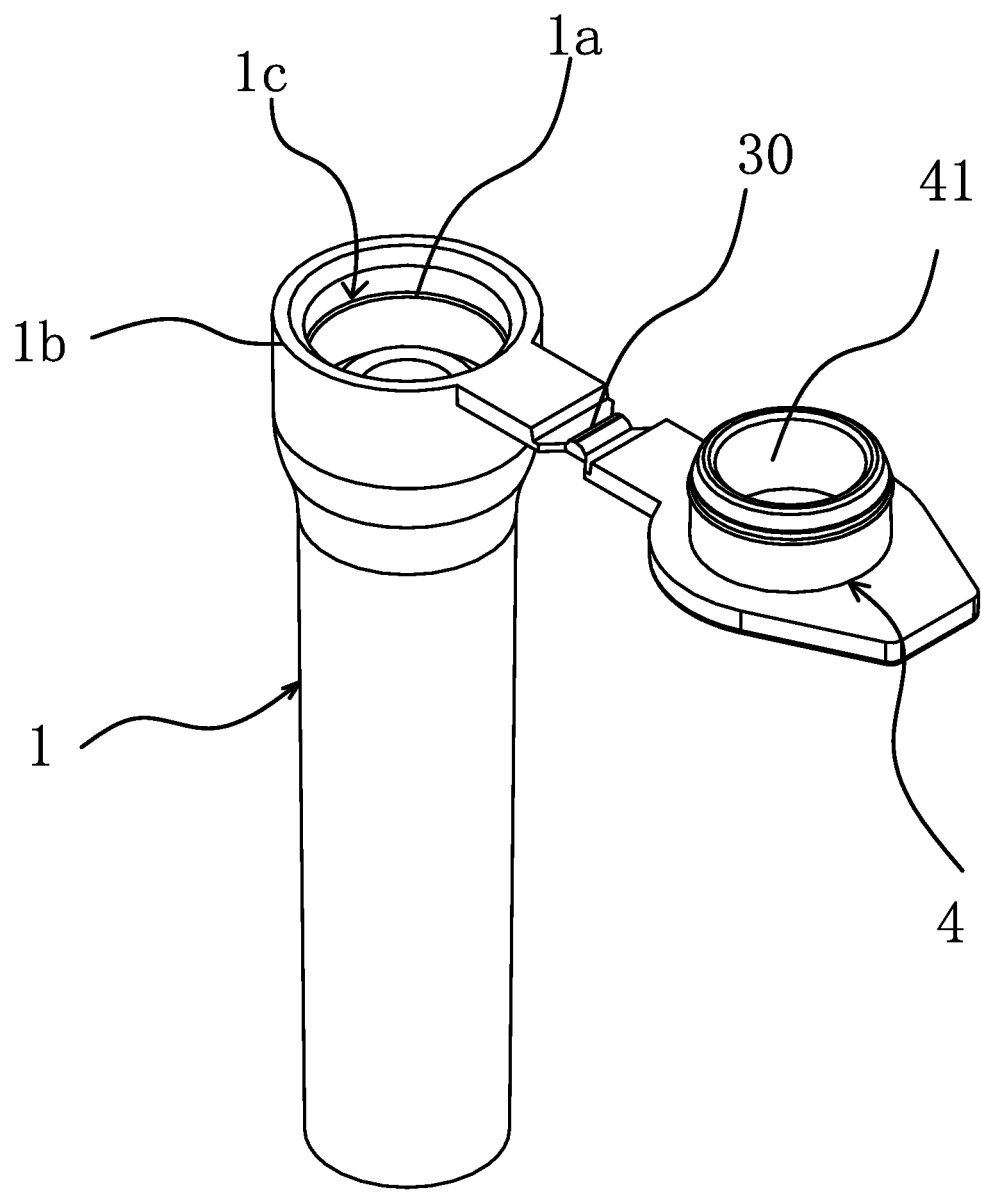
FIG. 1 is a structural diagram of one embodiment of a shock tube prior to the installation of a second electrode in embodiment 1.

By the following specific embodiments and accompanied figures, the technical solution of present invention will be more specifically described, but the present invention is not limited to these embodiments.

Embodiment 1

As shown in FIGS. 1, 2, 3, and 6, one embodiment of the shock tube comprises a tube 1, a first electrode 2, a second electrode 3 and a stopple 4. The stopple 4 and the tube 1 are connected by a flexible link 30. The tube 1 is internally provided with a cavity 1e for accommodating a target liquid sample. The first electrode 2 is arranged at one end of tube 1, and the other end of tube 1 is provided with an opening 1a interconnected with the cavity 1e. The working part of the first electrode 2 is interconnected with the cavity 1e. The edge of the opening 1a has an annular end surface. The second electrode 3 is arranged in the stopple 4, and the outer end of the second electrode 3 can be electrically connected with the exterior via an opening of the stopple 4. The inner end surface of the second electrode 3 can be well-matched with the annular end surface on the edge of opening 1a. An elastic piece is disposed between the stopple 4 and second electrode 3. The outer side surface of the elastic piece is abutting against or connected with the stopple 4, and the inner side surface of the elastic piece is abutting against the second electrode 3. The periphery of the opening 1a has a positioning structure which is capable of fixing the stopple 4 at the end of tube 1 and generating a compressive deformation to the elastic piece. The positioning structure comprises a connecting tube 1b which forms an integral body with the end part of the tube 1. The connecting tube 1b is provided with a chamber 1c for the stopple 4 to plug-in. The chamber wall of the chamber 1c has a first rib 1d. The outer side surface of the stopple 4 has a second rib 43 which can snap-connect with first rib 1d. In the present embodiment, the first rib 1d and second rib 43 are in complete annular shapes. They may also be in other shapes composed of several arcuate segments etc.

During operation, one embodiment of the shock tube can be filled up into the cavity 1e with a liquid sample comprising cells and materials to be injected into the cells, forming a bulged liquid surface, then the stopple 4 is secured to the end of tube 1 via a positioning structure to generate a compressive deformation to the elastic piece between the stopple 4 and the second electrode 3, while the second electrode 3 is pressed against the end surface of the opening 1a. The first electrode 2 and second electrode 3 are interconnected with the liquid in the cavity 1e. Then the first electrode 2 and second electrode 3 are connected with the pulse power supply. Electrification produces an electric field within the shock tube 20, causing the cell membranes to possess certain permeability, so that the target material in the liquid sample can enter the cells. When the stopple 4 is fixed to the end portion of the tube 1, a compressive deformation is generated in the elastic piece, to avoid the formation of gaps between the second electrode 3 and the opening 1a, improving the sealing performance between the second electrode 3 and the end surface of the opening 1a, thereby preventing air from entering the liquid sample in the cavity 1e. In addition, when the stopple 4 becomes slightly uptilted, the elastic piece can also make certain deformation recovery, to ensure the second electrode 3 to remain closely abutting with the end surface at the edge of opening 1a, so that still no air bubble will be generated in liquid sample in the cavity 1e when there is some operation deviation during sample loading by the experimenter, effectively improve sealing performance between the second electrode 3 and the opening 1a, thereby inhibiting ambient air from entering the cavity 1e when loading liquid sample.

In one embodiment, the tube 1 and stopple 4 are made of an insulating material. The first electrode 2 and second electrode 3 are made of an electrically conductive material. The first electrode 2 may either be directly fixed to the tube 1, or may be installed inside a stopple 4, as with the second electrode 3 before being used to seal the cavity 1e of tube 1. The elastic piece is an elastic piece 5 made of rubber and plastic materials. The stopple 4 comprises the pipe having a first through-hole 41. The second electrode 3 is plug-in to the first through-hole 41. The second electrode 3 comprises a rod 31 and a cap 32 which is fixedly connected to one end of the rod 31. The other end of the rod 31 can be electrically connected with the exterior via an opening of the stopple 4. The elastic piece 5 is socket-connected on the outer side surface of rod 31. The outer end of the stopple 4 has a retaining edge 42 radially extended inward along first through-hole 41. The outer end surface of the elastic piece 5 abuts against the retaining edge 42, and the inner end surface of the elastic piece 5 abuts against the cap 32. Rubber and plastic materials include plastics, rubber, silicone and the like. When the stopple 4 is fixed to the end of tube 1, the second electrode 3 is well-matched with end surface of the edge of opening 1a of cavity 1e of tube 1. The elastic piece 5 generates a compressive deformation to improve sealing effect of the second electrode 3 with end surface of the edge of opening 1a. The rod 31 can pass through the retaining edge 42 and extends to the exterior of the stopple 4 to facilitate the electrification of second electrode 3. Of course the second electrode 3 may also not extend to the exterior of the stopple 4. The external electrical connection contact is in contact with the end of second electrode 3 to achieve electrical connection. The elastic piece 5 may be generally made into complete ring-shape and may be an incomplete ring, as long as it is resilient and capable of being plugged with the second electrode 3.

In one embodiment, the elastic piece 5 may be a separate elastic piece 5 mounted in first through-hole 41 with an interference fit method, or mounted in first through-hole 41 by bonding or other methods. A first retaining shoulder 33 is provided between the elastic piece 5 and the cap 32. The first retaining shoulder 33 may be made into ring-shape and disposed on the same axis as elastic piece 5 and cap 32. The size or diameter of the first retaining shoulder 33 is larger than the diameter of rod 31 and smaller than the diameter of cap 32. First retaining shoulder 33 may also have an incomplete ring shape or other shapes. Its size or spatial dimension has to be larger than the diameter of rod 31 and smaller than the diameter of cap 32. The first retaining shoulder 33 separates the cap 32 from the elastic piece 5, causing the cap 32, in compressing the elastic piece 5, has to apply stress through the first retaining shoulder 33. The diameter or size of first retaining shoulder 33 is smaller than the cap 32 and elastic piece 5, thereby producing relatively greater pressure on a small contact area, prompting easy deformation and displacement of elastic piece 5. When the stopple 4 is fixed in the positioning structure, the second electrode 3 is well-matched with end surface of the opening 1a. The elastic piece 5 is in compressed state under pressure from the second electrode 3. Pressure is generated by this compressive deformation and exerted to end surface of opening 1a at end of tube 1 to improve sealing performance, and when the stopple 4 is slightly uptilted, a certain deformation recovery will be generated to maintain the pressing of second electrode 3 against the end surface of opening 1a at end of tube 1.

The first retaining shoulder 33 is a separate component. The first retaining shoulder 33 is socket-fitted on the rod 31 between the elastic piece 5 and the cap 32. Its material may be an insulator or non-insulator. The outer side surface of elastic piece 5 is well-matched with the inner wall of first through-hole 41 and forms a seal. The inner side surface of elastic piece 5 is well-matched with the outer side surface of rod 31 and forms a seal.

The first rib 1d and second rib 43 may be of a complete annular-shape or discontinuous annular shape. A snap-connection effect can be achieved in both cases. The protrusions of first rib 1d and second rib 43 may not be obvious. A stopple 4 of size slightly larger than the internal size of the connecting tube 1b is used to insert into the tube 1 portion, to achieve the purpose of positioning by interference fit method. The stopple 4 is snap-connected with the connecting tube 1b, making both connection and separation of the two very easy, to enhance the convenience in liquid injection and pipetting after the completion of electroporation. Of course the threaded connection method may also be used. While using threaded connection, the stopple 4 can be fixed to the connecting tube 1b by rotating it. As alternative case, the positioning structure may be a first strike disposed on the stopple 4 and a first latch disposed on tube 1 which can snap-connect with the first strike.

Figure 2:
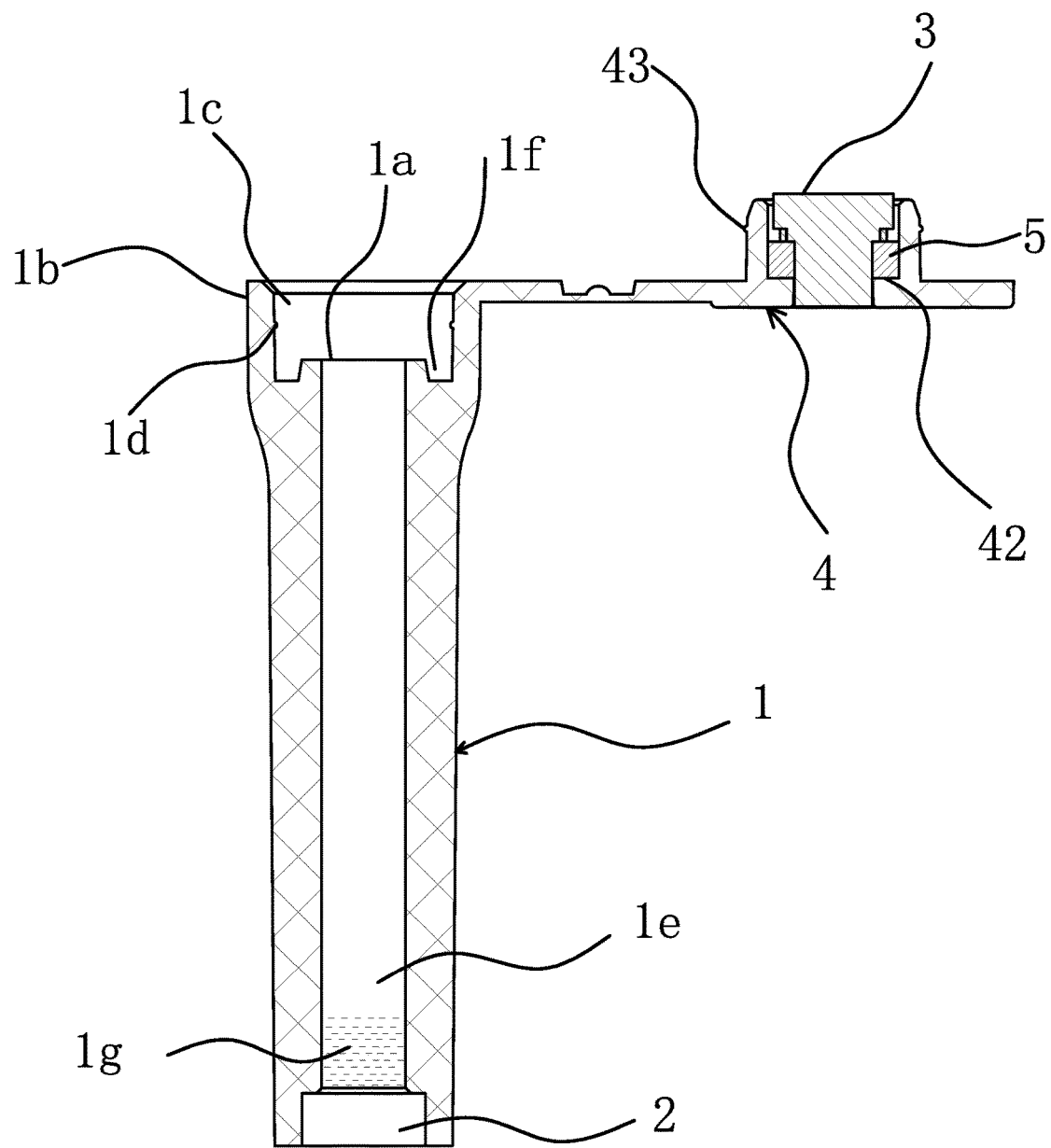
FIG. 2 is a cross-sectional diagram of one embodiment of a shock tube prior to the fixing of a stopple in a positioning structure in embodiment 1.
Figure 3:
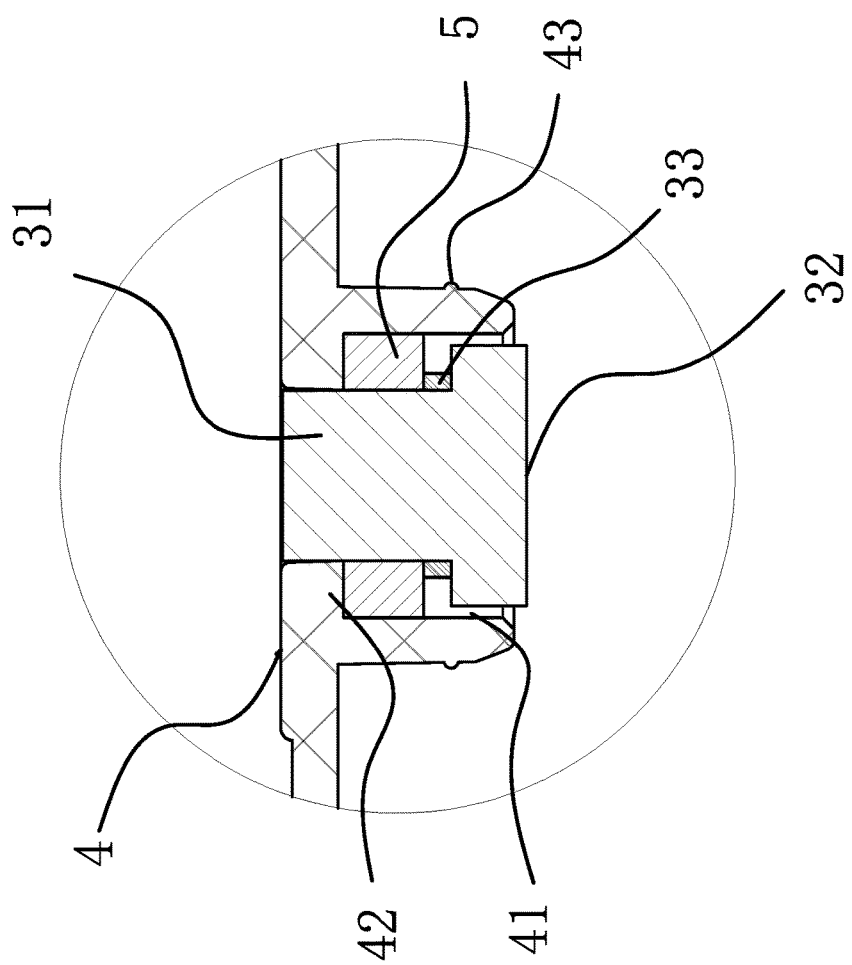
FIG. 3 is a partial enlargement diagram of embodiment 1.

As shown in FIG. 2, in one embodiment, the end surface at edge of the opening 1a of tube 1 has an annular groove 1f. The cavity 1e is filled up with a liquid sample until a bulged surface is formed on the opening 1a. Then the second electrode 3 is in contact with the bulged liquid surface and presses downward to seal the opening 1a. The excess liquid of bulged surface is squeezed and flows into the annular groove 1f, without affecting the cell electroporation process in liquid sample in the cavity 1e.

As shown in FIG. 2, the cavity 1e of tube 1 is provided with an ion conductive layer 1g. The bottom layer surface of the ion conductive layer 1g is in contact with a first electrode 2. The upper layer surface of the ion conductive layer 1g is capable of contacting with the target liquid sample. The cell sample is separated from direct contact with the first electrode 2 by ion conductive layer 1g, so as to avoid direct damage to the cell sample by electrochemical reaction near the first electrode 2. The ion conductive layer 1g contains components of a soluble salt as the ion source, which infiltrates the salt solution and forms conductive ions.

Embodiment 2

Figure 4:
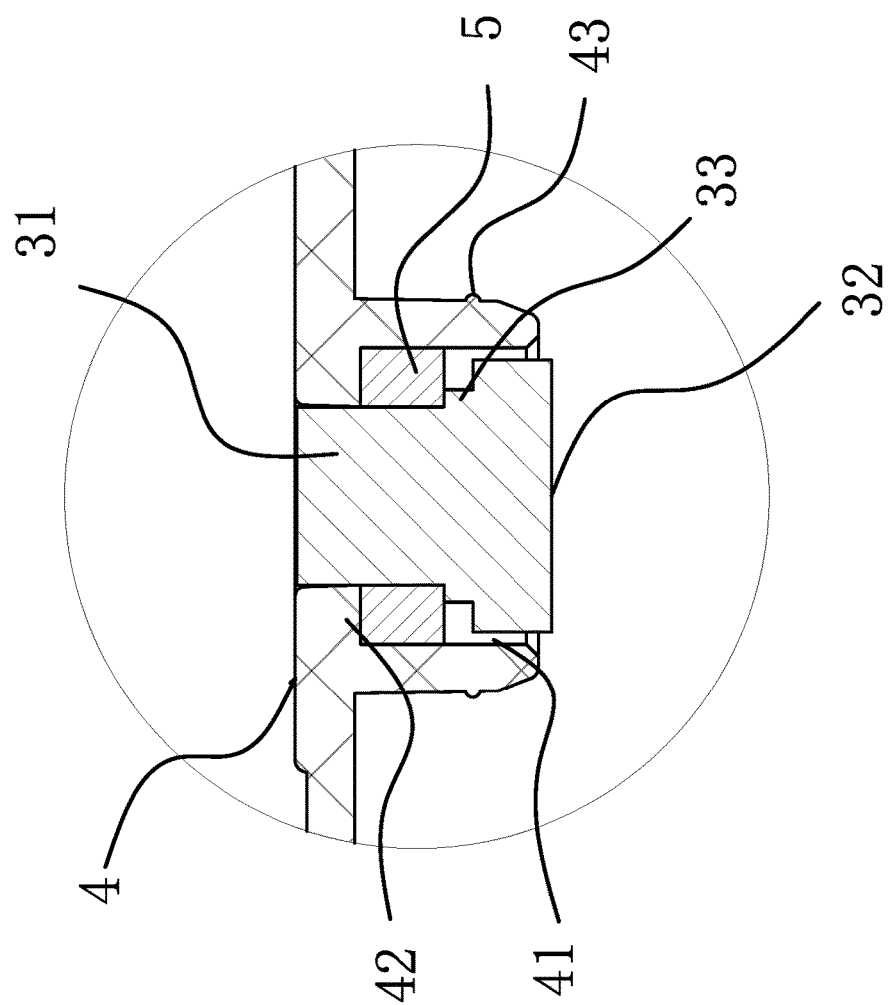
FIG. 4 is a partial enlargement diagram of embodiment 2.

As shown in FIG. 4, the present embodiment is substantially the same as Embodiment 1, except the following. The first retaining shoulder 33 forms an integral body with the cap 32 and rod 31. The inner end surface of elastic piece 5 abuts against the end surface of first retaining shoulder 33. When the rod 31 is plugged inelastic piece 5, the cap 32 and elastic piece 5 are separated by and mutually exert stresses through first retaining shoulder 33. The first retaining shoulder 33 may be in annular shape, discontinuous annular shape, polygonal shape or other shapes. Its size or diameter is larger than the diameter of rod 31 and smaller than the diameter of cap 32.

Embodiment 3

Figure 5:
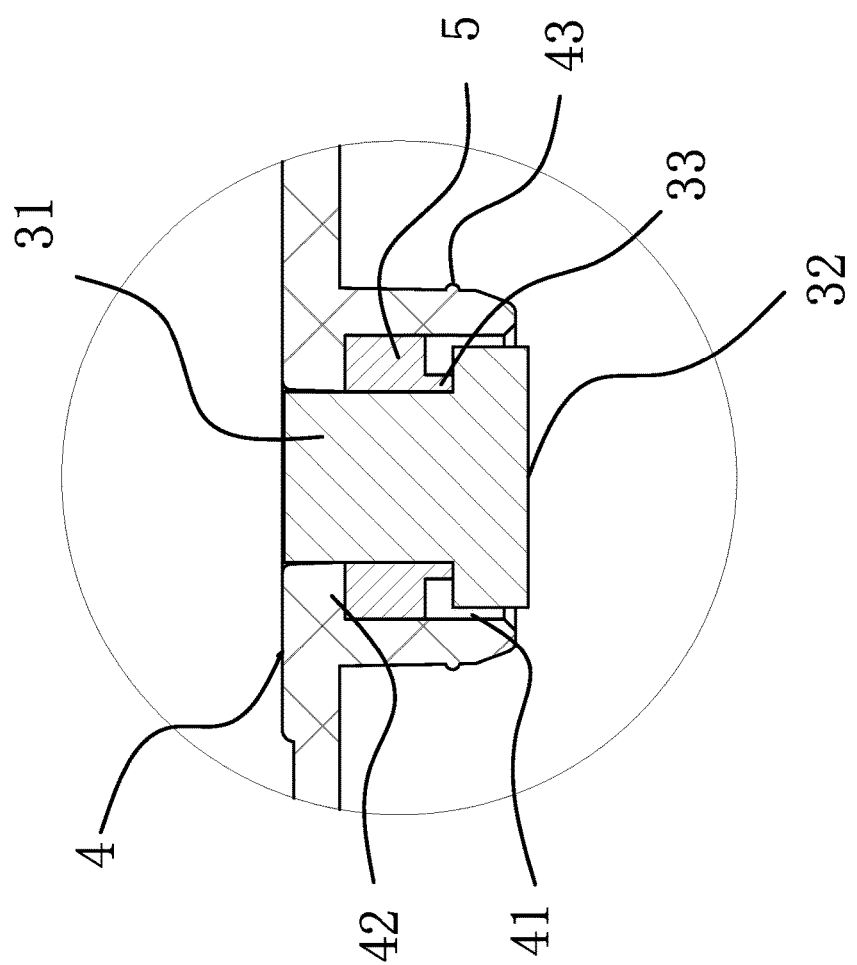
FIG. 5 is a partial enlargement diagram of embodiment 3.
Figure 6:
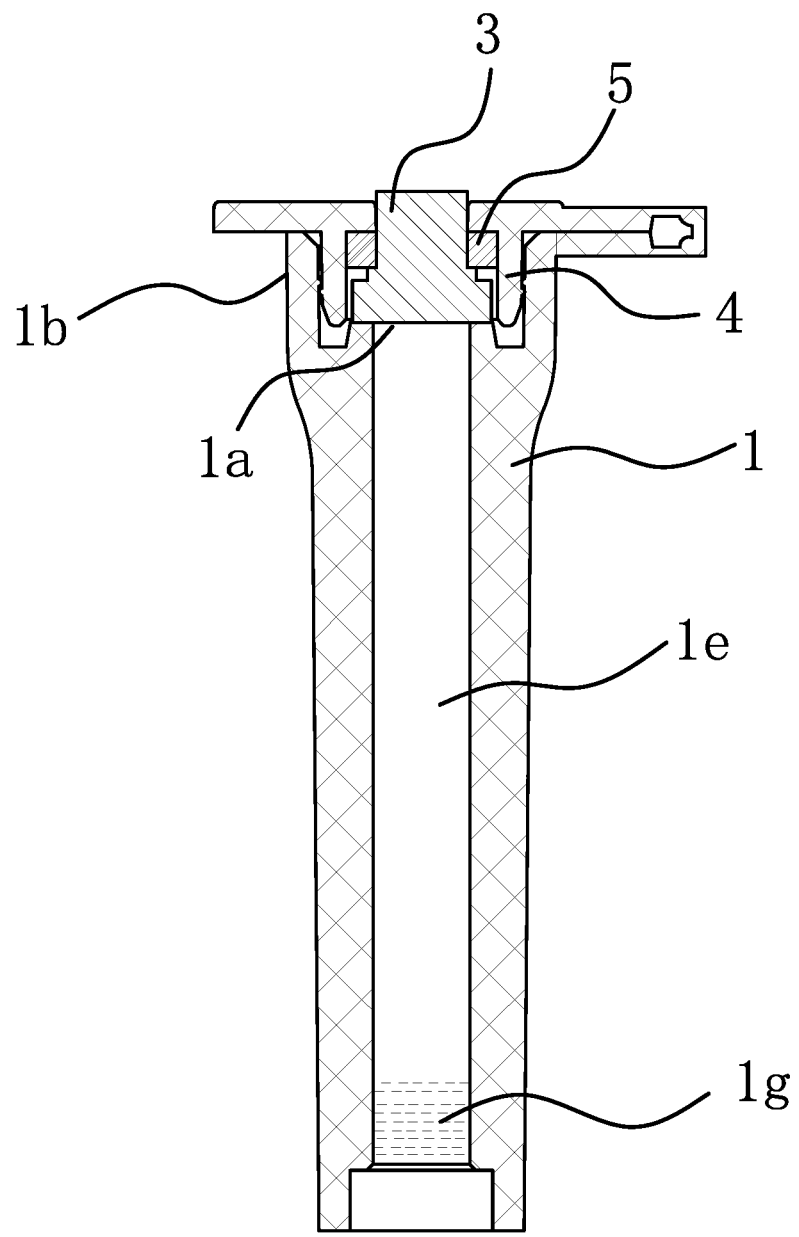
FIG. 6 is a cross-sectional diagram of one embodiment of a shock tube when a second electrode together with a stopple is fixed in a positioning structure.

As shown in FIG. 5, the present embodiment is substantially the same as Embodiment 1 or Embodiment 2, except the following. The first retaining shoulder 33 is fixedly arranged on the elastic piece 5 or the first retaining shoulder 33 forms an integral body with the elastic piece 5. The first retaining shoulder 33 abuts against the cap 32. The first retaining shoulder 33 may be in annular shape, discontinuous annular shape, polygonal shape or other shapes. Its size or diameter is larger than the diameter of rod 31 and smaller than the diameter of cap 32.

Embodiment 4

Figure 7:
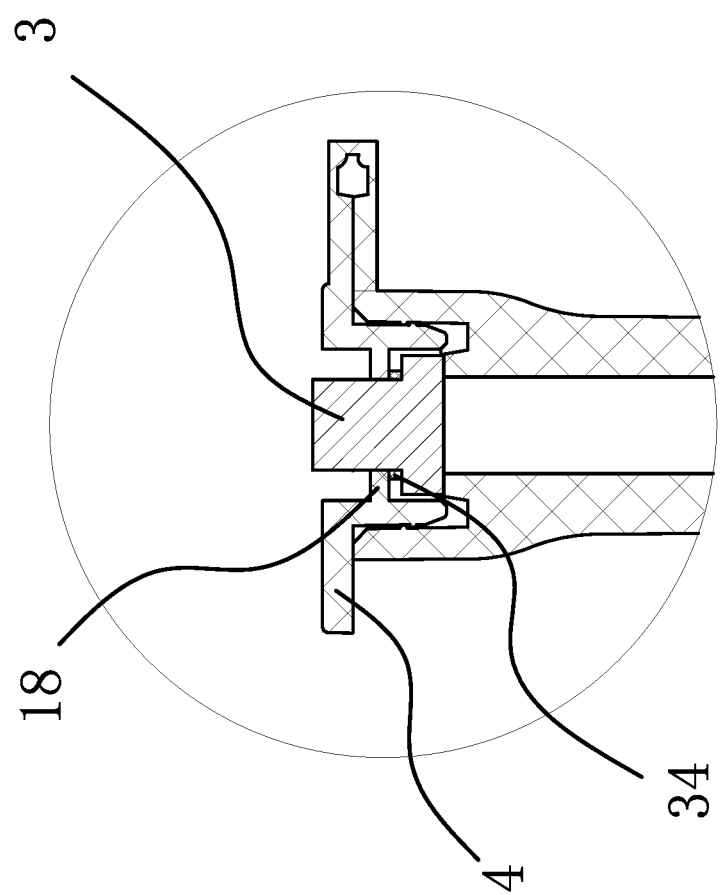
FIG. 7 is a partial enlargement diagram of embodiment 4.

As shown in FIG. 7, the present embodiment is substantially the same as Embodiment 1, except the following. An alternative solution is provided for elastic piece in the present embodiment. The elastic piece is a resilient retaining edge elastic piece 18 extended inward along first through-hole 41 on inner wall of the first through-hole 41. The retaining edge elastic piece 18 abuts against the outer side surface of the rod 31 and forms a seal. A second retaining shoulder 34 is also provided between the retaining edge elastic piece 18 and the cap 32. The second retaining shoulder 34 is disposed separately. The second retaining shoulder 34 may be fabricated into ring shape and disposed on the same axis as the retaining edge elastic piece 18 and the cap 32. The diameter of the second retaining shoulder 34 is larger than the diameter of rod 31 and smaller than the diameter of cap 32. The second retaining shoulder 34 may also be in incomplete ring shape or other shapes. Its size or spatial dimension is larger than the diameter of rod 31 and smaller than the diameter of cap 32. The material of retaining edge elastic piece 18 is the same as stopple 4. The outer side forms an integral body with inner wall of the body of the stopple 4, and an opening is formed in the center. The rod 31 of second electrode 3 is plug-in to the opening of retaining edge elastic piece 18 by interference fit or bonding method. Due to precision requirement of the body of shock tube 20, it is generally necessary to be manufactured with certain strength to prevent deformation. As an elastic piece, the retaining edge elastic piece 18, which forms an integral body with the stopple 4, may use the strength reduction design there to gain flexibility, such as designing a thinner portion than the other portions, so that it is more prone to pressure deformation. The retaining edge elastic piece 18 may generally be made into a complete ring shape, or it may be an incomplete ring in shape, all acceptable as long as it is flexible and can be plugged with the second electrode 3.

Embodiment 5

Figure 8:
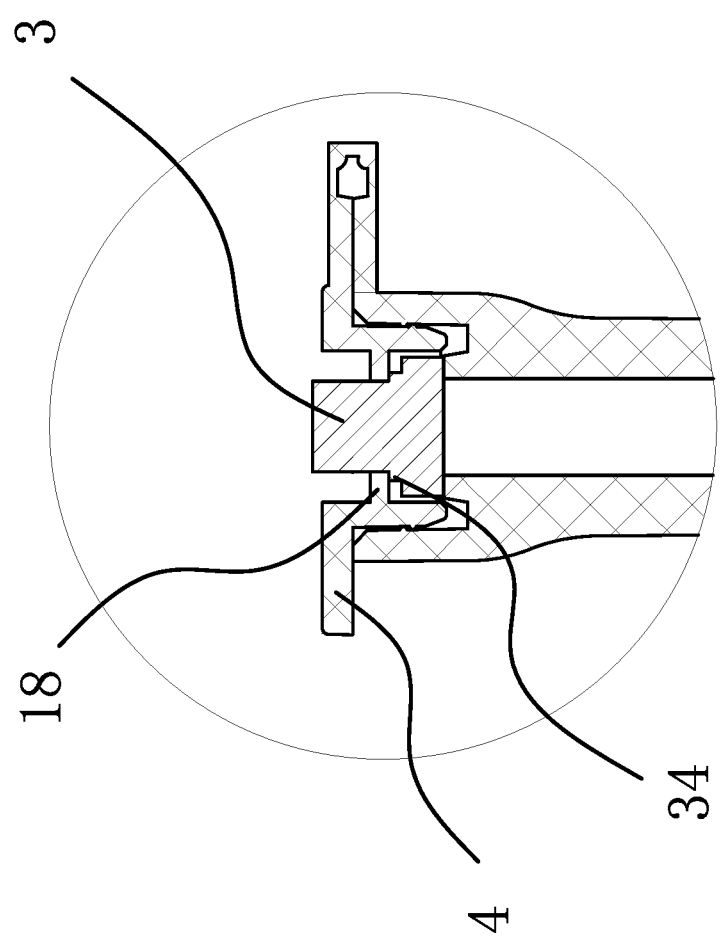
FIG. 8 is a partial enlargement diagram of embodiment 5.

As shown in FIG. 8, the present embodiment is substantially the same as Embodiment 4, except the following. The second retaining shoulder 34 forms an integral body with the cap 32 and rod 31 in the present embodiment. The inner end surface of the retaining edge elastic piece 18 abuts against the end surface of the second retaining shoulder 34. The second retaining shoulder 34 may be in annular shape, discontinuous annular shape, polygonal shape or other shapes. Its size or diameter is larger than the diameter of rod 31 and smaller than the diameter of cap 32.

Embodiment 6

Figure 9:
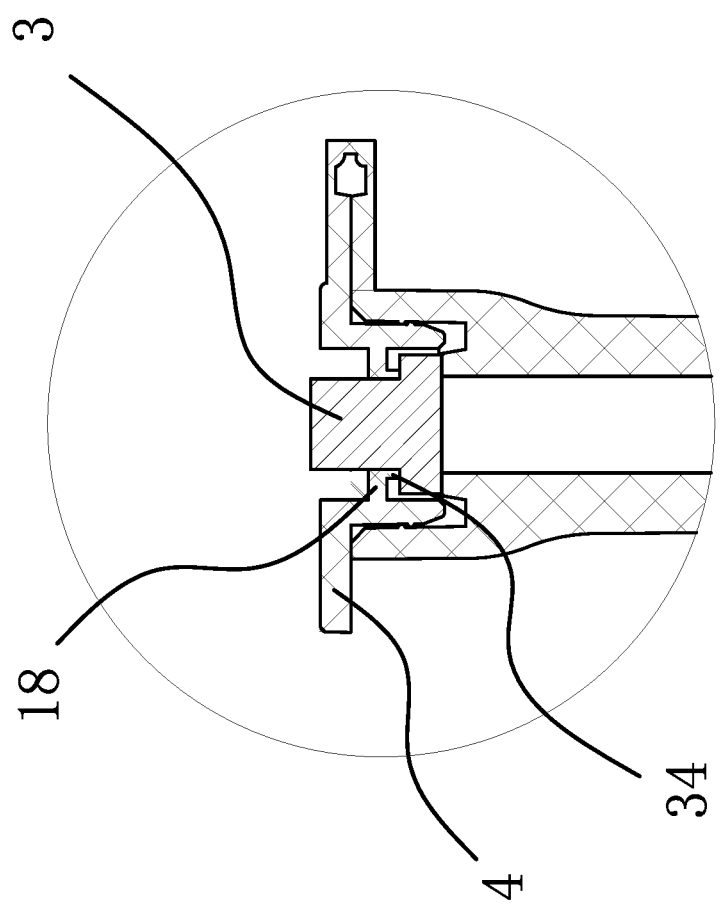
FIG. 9 is a partial enlargement diagram of embodiment 6.

As shown in FIG. 9, the present embodiment is substantially the same as Embodiment 4 or Embodiment 5, except the following. The second retaining shoulder 34 forms an integral body with the retaining edge elastic piece 18 in the present embodiment. The second retaining shoulder 34 abuts against the cap 32. The second retaining shoulder 34 may be in annular shape, discontinuous annular shape, polygonal shape or other shapes. Its size or diameter is larger than the diameter of rod 31 and smaller than the diameter of cap 32.

Embodiment 7

Figure 10:
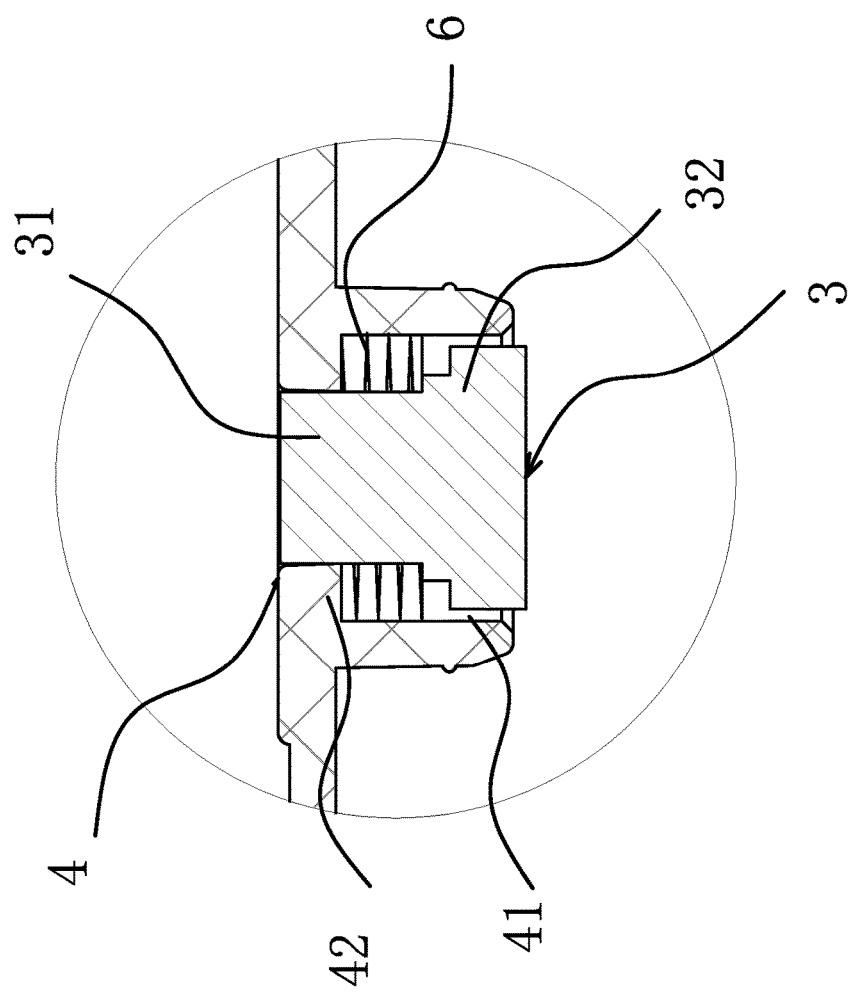
FIG. 10 is a partial enlargement diagram of embodiment 7.

As shown in FIG. 10, the present embodiment is substantially the same as Embodiment 1, except the following. As a solution for third type of elastic piece, the elastic piece in the present embodiment is a compression spring 6. The stopple 4 comprises a pipe having a first through-hole 41. The second electrode 3 is disposed in the first through-hole 41. The second electrode 3 comprises a rod 31 and a cap 32. One end of the rod 31 is fixedly connected with the cap 32. The other end of the rod 31 can be electrically connected with the exterior via an opening of the stopple 4. The compression spring 6 is socket-connected on the outer side surface of the rod 31. The outer end of the stopple 4 has a retaining edge 42 radially extended inward along the first through-hole 41. The outer end surface of the compression spring 6 abuts against the retaining edge 42, and the inner end surface of the compression spring 6 abuts against the cap 32. When the stopple 4 is fixed to the end part of tube 1, the compression spring 6 can generate a deformation compression to improve the sealing performance between the second electrode 3 and the end part of tube 1 at the edge of opening 1a.

Embodiment 8

As shown in FIG. 11 to FIG. 15, the present embodiment provides a cell electroporation device with a shock tube 20, wherein the cell electroporation device comprises a housing 7. The housing 7 is disposed with a fixing base 8 inside. The fixing base 8 is provided with a socket 821. The cell electroporation device also comprises a shock tube 20 which is plug-in to the socket 821. The shock tube 20 comprises a tube 1, a first electrode 2, a second electrode 3 and a stopple 4, wherein the tube 1 is internally provided with a cavity 1e for accommodating a target liquid sample. The first electrode 2 is arranged at one end of the tube 1, and the other end of tube 1 is provided with an opening 1a interconnected with the cavity 1e. The working part of the first electrode 2 is interconnected with the cavity 1e. The edge of the opening 1a has an annular end surface. The second electrode 3 is arranged in the stopple 4, and the outer end of the second electrode 3 can be electrically connected with the exterior via an opening of the stopple 4. The inner end surface of the second electrode 3 can be well-matched with the annular end surface of the edge of opening 1a. An elastic piece is arranged between the stopple 4 and the second electrode 3. The outer side surface of elastic piece abuts against or connects with the stopple 4, and inner side surface of the elastic piece abuts against the second electrode 3. The periphery of opening 1a has a positioning structure which is capable of fixing the stopple 4 at the end portion of tube 1 generating a compressive deformation to the elastic piece. The inner end of the socket 821 has a first electrode terminal 10 which can be electrically connected to the first electrode 2. The housing 7 is provided with a cover 9 for covering the outer end of socket 821. The cover 9 is disposed with a second electrode terminal 11 which can be electrically connected with the second electrode 3. The housing 7 is also provided with a power module 27 which is electrically connected to the first electrode terminal 10 and second electrode terminal 11.

During operation, one embodiment of the cell electroporation device can be filled up into the cavity 1e of tube 1 with a liquid sample and then covered with stopple 4. After the shock tube 20 is placed in the socket 821, the cover 9 is closed, so the first electrode terminal 10 is electrically connected to the first electrode 2, and the second electrode terminal 11 is electrically connected to the second electrode 3, and the pulse power is turned on to supply electricity, producing an electric field within the shock tube 20, enabling the injection of extracellular substances into the cells. Since the stopple 4 is also provided with an elastic piece for enhancing the action force between the second electrode 3 and the end surface of opening 1a, thus inhibiting gap formation between the second electrode 3 and the opening 1a. In addition, when the stopple 4 becomes slightly uptilted, the elastic piece can also make certain deformation recovery, to ensure the second electrode 3 to remain closely abutting with the end portion of tube 1 at end surface of opening 1a, thus inhibiting ambient air from entering the cavity 1e. Meanwhile, the internal generation of air bubbles by electrochemical reaction in the shock tube 20 during electroporation process can also be restrained. In summary, the shock tube 20 of the cell electroporation device can effectively improve sealing performance between the second electrode 3 and the end surface of opening 1a, thus inhibiting ambient air from entering the cavity 1e of the shock tube 20 and generates air bubbles and influence the electroporation, during the electroporation preparation process, reduce the influence of air bubbles generated by electrochemical reaction on electric current during the electroporation process, thereby improving the electroporation performance of the cell electroporation device.

Figure 11:
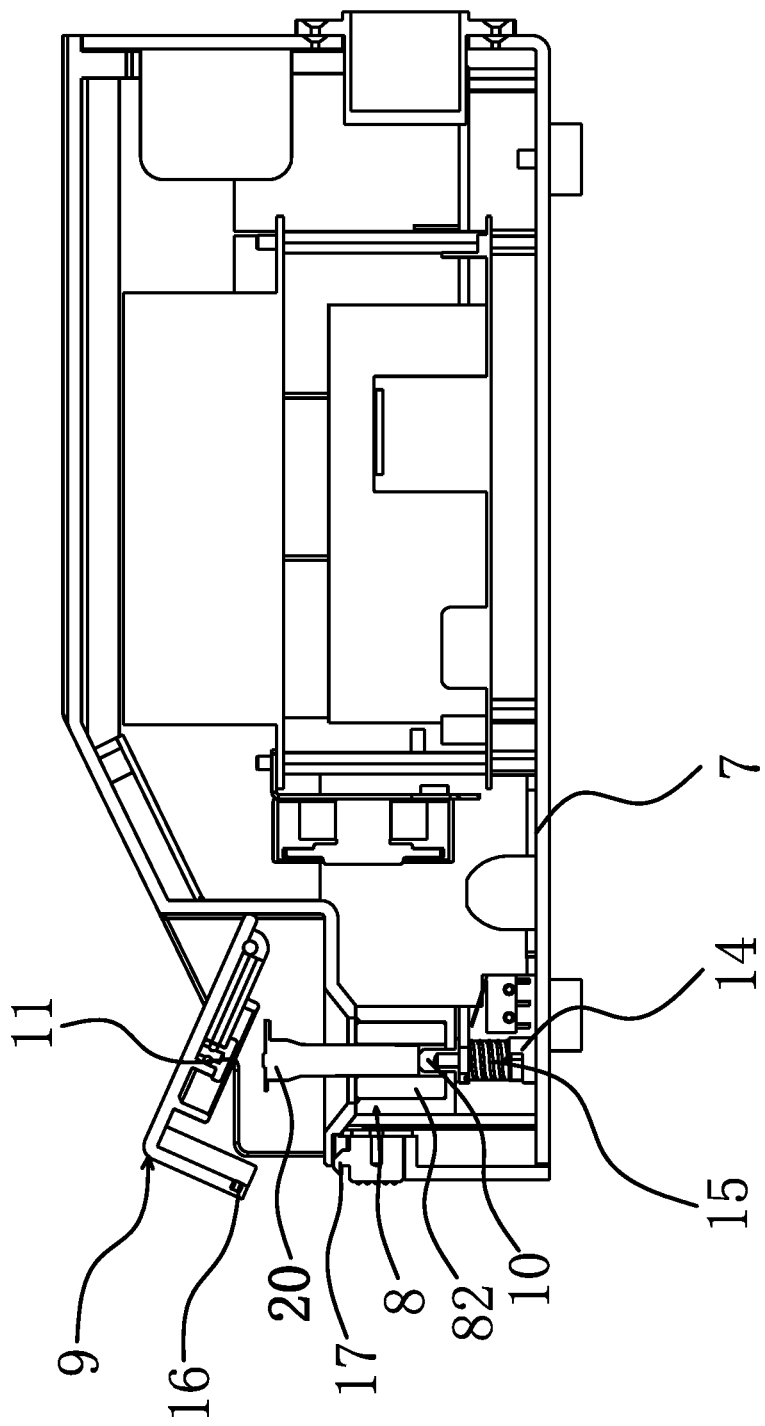
FIG. 11 is a structural diagram of one embodiment of a cell electroporation device in embodiment 8.
Figure 12:
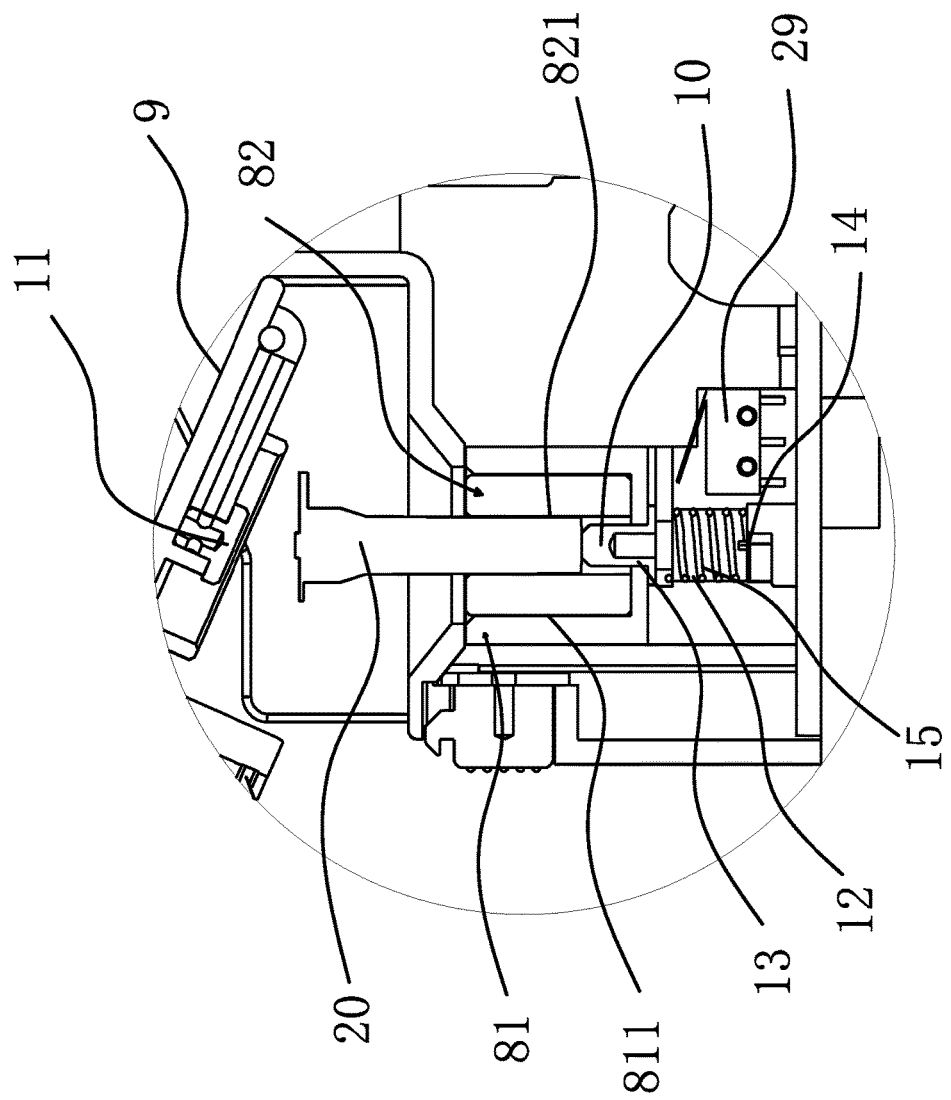
FIG. 12 is a partial enlargement diagram of embodiment 11.
Figure 13:
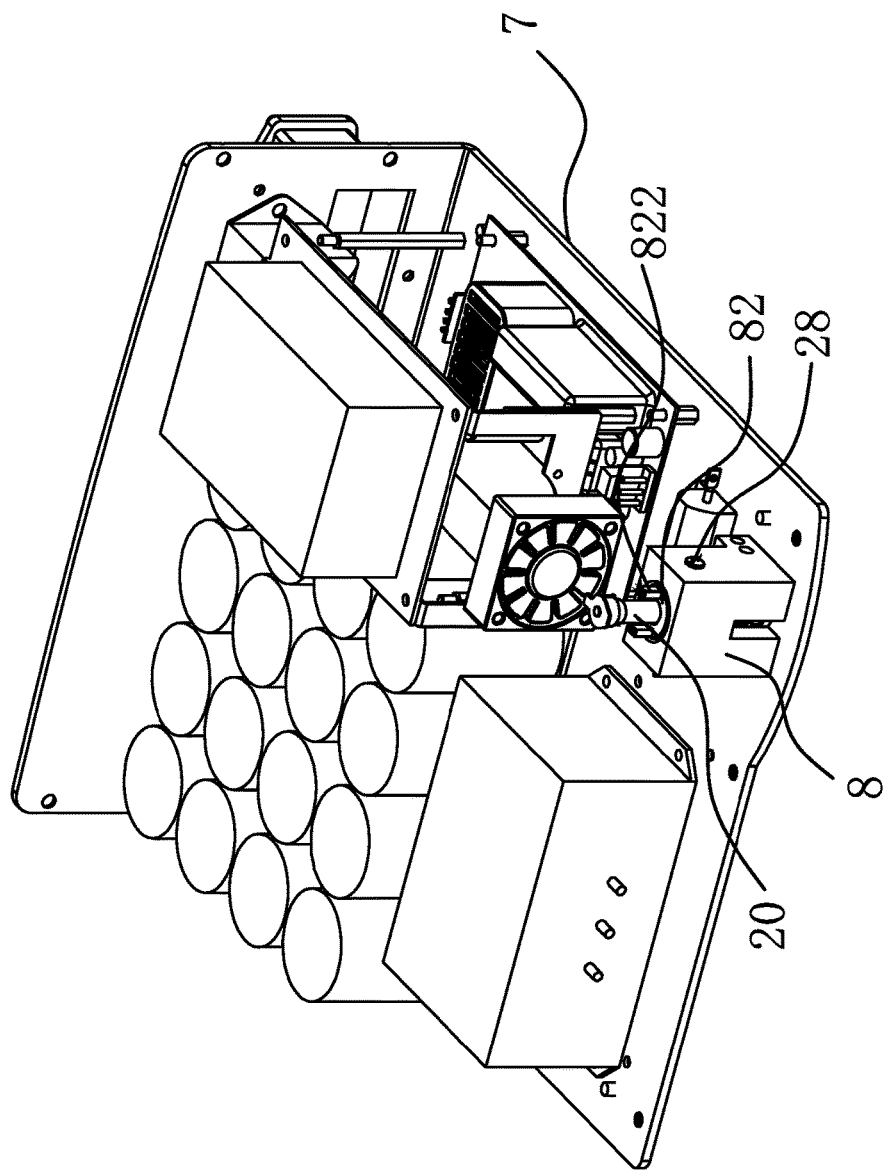
FIG. 13 is an exploded diagram of one embodiment of a cell electroporation device in embodiment 8.
Figure 14:
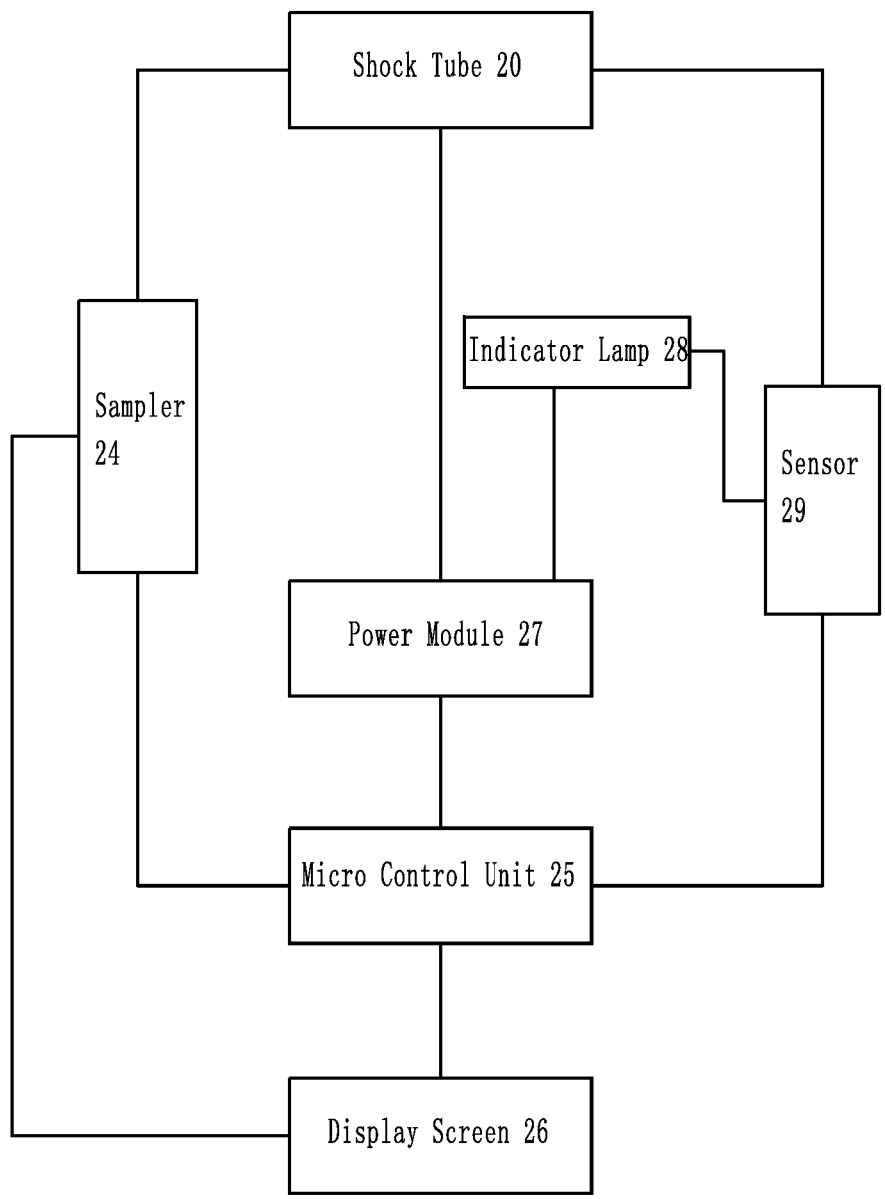
FIG. 14 is a working principle diagram of one embodiment of a cell electroporation device in embodiment 8.
Figure 15:
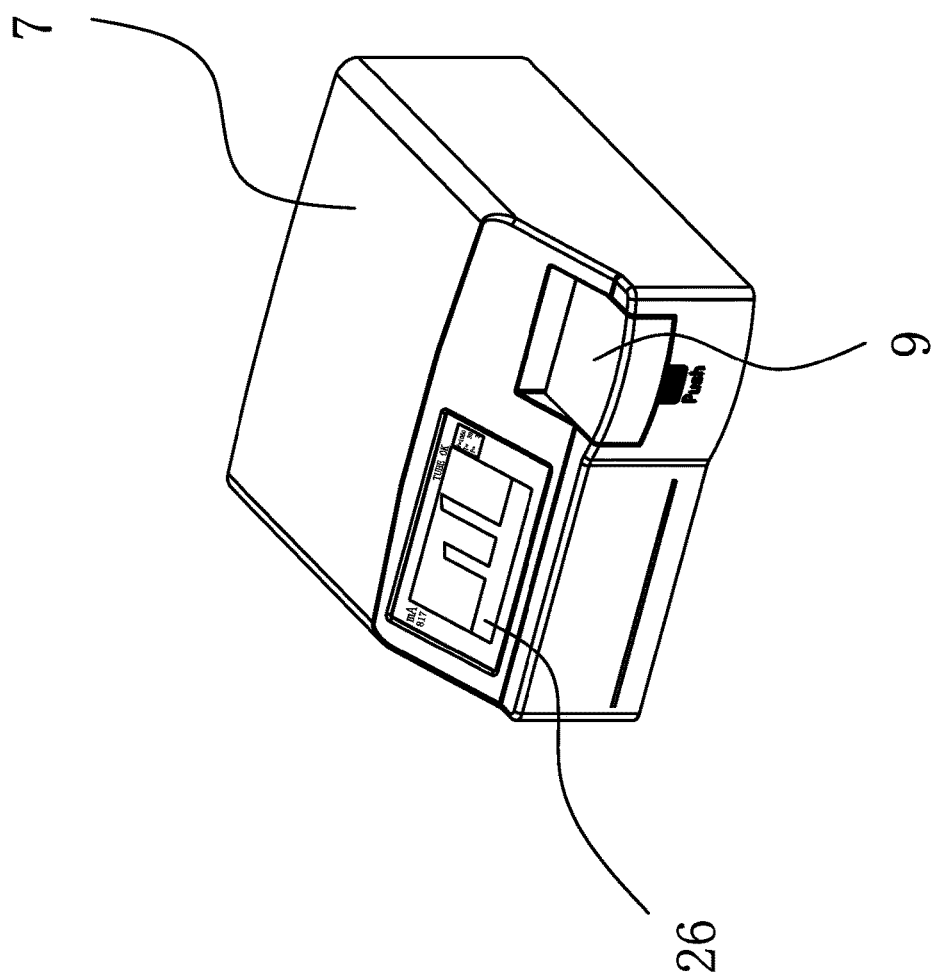
FIG. 15 is an axonometric diagram of one embodiment of a cell electroporation device in embodiment 8.

As shown in FIGS. 11, 12, and 13, one embodiment of the fixing base 8 comprises a seat 81 and a clamping cylinder 82. The socket 821 is disposed inside the clamping cylinder 82. A silo 811 is provided in the seat 81. The clamping cylinder 82 is inserted in the silo 811 and both are removable and interconnected. The bottom of the clamping cylinder 82 abuts with the bottom of the silo 811. The top end of clamping cylinder 82 is provided with at least one handle 822.

As shown in FIG. 12, one embodiment of the seat 81 contains also a hollow 12. The silo 811 has a second through-hole 13 at its bottom. The two ends of the second through-hole 13 are connected with the socket 821 and hollow 12 respectively. The hollow 12 is provided with a spring seat 14 and a spring 15. The inner end of spring 15 is fixed to the spring seat 14, and the outer end of spring 15 is connected to the inner end of the first electrode terminal 10. The outer end of the first electrode terminal 10 can pass through the second through-hole 13 and inserted in the socket 821. After the spring seat 14 and spring 15 are provided in the design, when the socket 821 opening 1a is closed by the cover 9, the first electrode 2 and second electrode 3 can be connected to the first electrode terminal 10 and second electrode terminal 11 respectively. When the shock tube 20 is pressed by the cover 9, the spring 15 is compressed and a greater extra pressure is generated. This pressure is exerted through the second electrode 3 to the opening 1a of cavity 1e, enhancing the sealing performance of second electrode 3 and opening 1a of cavity 1e. During the cell electroporation process, due to the electrochemical reaction, the electrolysis process will produce some air bubbles. When the pressure between the second electrode 3 and the opening 1a of cavity 1e becomes higher, these electrochemical air bubbles will be compressed and its influence to the distribution of electric current in the electroporation process will be reduced, thereby increasing cell electroporation effect. After the completion of cell electroporation, when the cover 9 is opened, the shock tube 20 may pop up partially from the socket 821 under the action of the spring 15, making it convenient to pick it up.

The inner end of the cover 9 is hinged to the housing 7. Outer end of the cover 9 is provided with a second latch 16. The housing 7 is also provided with a second strike 17 which can snap-connect with the second latch 16. The clamping cylinder 82 and cover 9 are made of a material with light transmittance greater than 50%. The accessory of seat 81 is internally provided with a sensor 29 for detecting the displacement change of shock tube 20. The housing 7 is provided inside with a micro control unit 25. The micro control unit 25 is electrically connected with the sensor 29. The seat 81 is also provided inside with an indicator lamp 28 which is electrically connected with micro control unit 25. The indicator lamp 28 is also connected with the power module 27. In addition to the function of indicating the connection status of shock tube 20, the indicator lamp 28 can also serve the function of illumination. A brighter light source such as LED light can be used to illuminate the shock tube 20. The sensor 29 can be a mechanical trigger switch. The switch will be triggered by its linkage bar when displacement of first electrode terminal 10 occurs. The sensor 29 can also be a photoelectric switch. The photoelectric switch will be triggered by an affected optical path when displacement of first electrode terminal 10 occurs. The sensor 29 can also be a Hall switch etc., triggered when displacement of the shock tube 20 or first electrode terminal 10 occurs.

The indicator lamp 28 is mounted on housing 7 near the shock tube 20 socket 821, providing lights to illuminate the shock tube 20 nearby. Alternatively, the indicator lamp 28 can also be mounted on the fixing base 8. A transverse through-hole may be provided on the fixing base 8 to install the indicator lamp 28. The clamping cylinder 28 can be made of a transparent material. The indicator lamp 28 on the fixing base 8 may be used to illuminate the shock tube 20 laterally through the clamping cylinder 82, achieving a clearer visual effect. The housing 7 is provided with a display screen 26. The housing 7 is internally provided with a sampler 24. The micro control unit 25 is electrically connected with display screen 26 and power module 27. The sampler 24 is electrically connected with shock tube 20 and micro control unit 25 respectively. Power supply module 27 can generate electric pulses required in cell electroporation. The display screen 26 is used for displaying instrumental and experimental information as well as display the experiment operation interface. The micro control unit 25 can control the power module 27 and display screen 26. The micro control unit 25 includes a programmable single-chip microcomputer and other microprocessors etc. The sampler 24 can collect electrical signals in cell electroporation process, including voltage or current signals. The sampler 24 includes resistors and other electronic components. Electrical signals are being processed via the micro control unit 25, and related parameters can be displayed in the form of data values or wave curves on the display screen 26.

Embodiment 9

Figure 16:
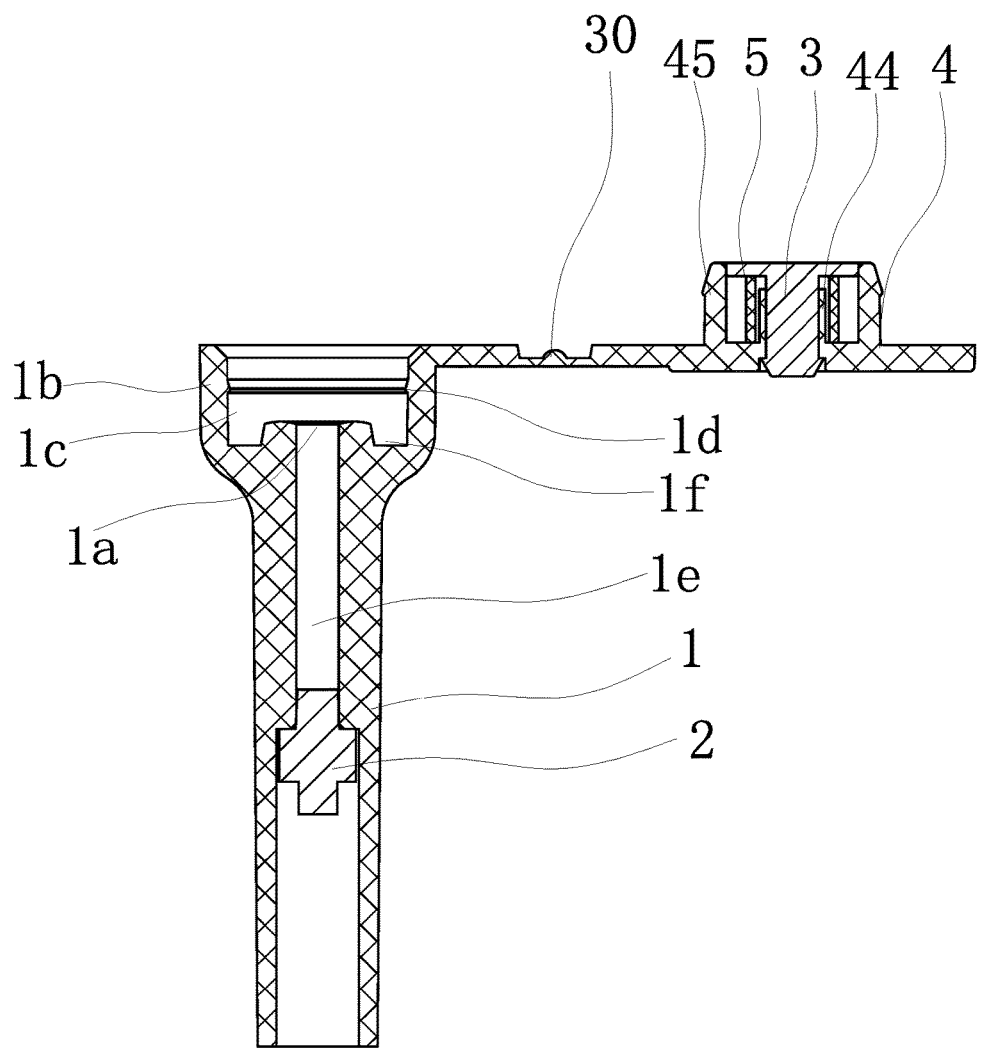
FIG. 16 is a cross-sectional diagram of one embodiment of a shock tube when, together with a stopple, a second electrode is fixed in a positioning structure in embodiment 9.
Figure 17:
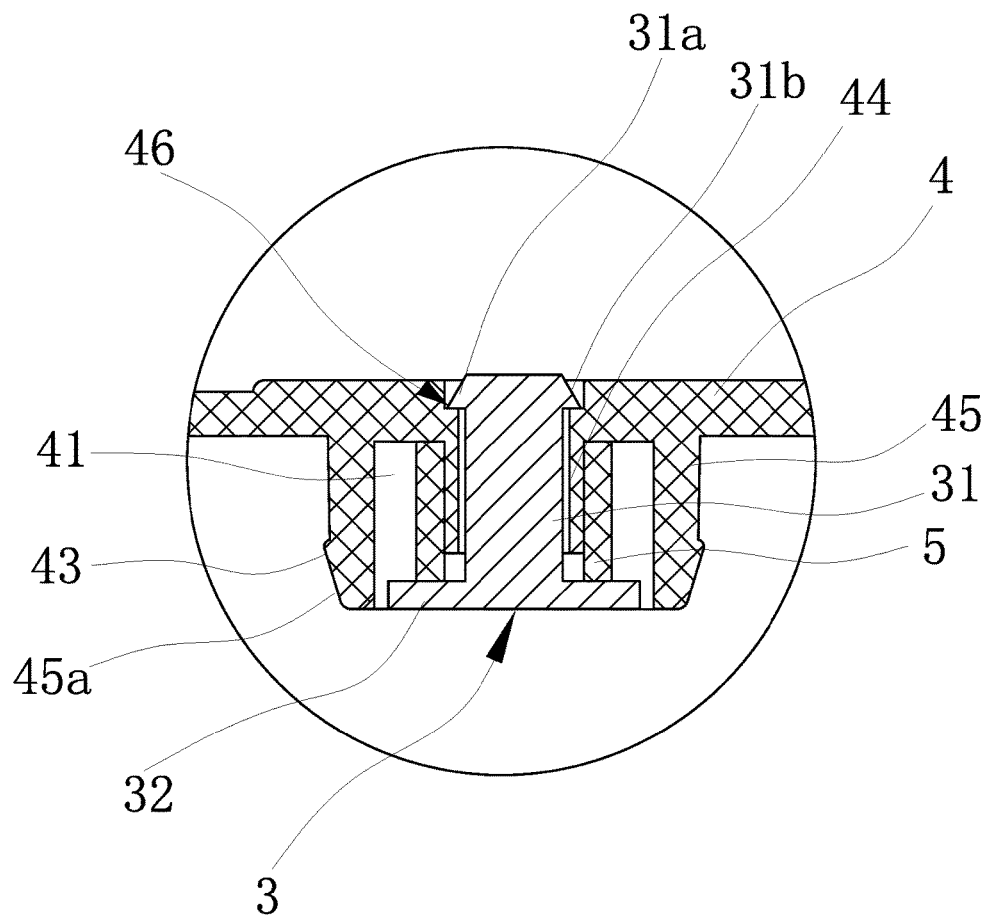
FIG. 17 is a partial enlargement diagram of embodiment 9.

As shown in FIGS. 16 and 17, one embodiment of the shock tube comprises a tube 1 and a stopple 4. The stopple 4 is connected to the tube 1 via a flexible link 30. The tube 1 is internally provided with a cavity 1e for accommodating a target liquid sample. The first electrode 2 which is connected with cavity 1e is arranged at one end or middle part of the tube 1, and the other end of the tube 1 is provided with an opening 1a interconnected with the cavity 1e. The end surface at edge of the opening 1a has an annular groove 1f. The second electrode 3 is arranged in the stopple 4, and the outer end of the second electrode 3 can be electrically connected with the exterior via an opening of the stopple 4. The second electrode 3 is slidably connected to the stopple 4. The inner end surface of the second electrode 3 can be well-matched with the annular end surface of the edge of opening 1a, characterized in that, the stopple 4 comprises a pipe 45 having a first through-hole 41 and a tubular mounting seat 44 located in the pipe 45. The second electrode 3 is slidably connected on the mounting seat 44 and an annular elastic piece 5 is socket-fitted outside the mounting seat 44. The height of elastic piece 5 is greater than the height of mounting seat 44. The height of pipe 45 of the stopple 4 is greater than the height of the elastic piece 5. When the stopple 4 is fixed to the end portion of tube 1, the elastic piece 5 generates a compressive deformation, causing upper end surface of elastic piece 5 abuts against the stopple 4 and lower end surface of elastic piece 5 abuts against the second electrode 3. During operation, the shock tube can be filled up into the cavity 1e from opening 1a of tube 1 with a liquid sample comprising cells and materials to be injected into the cells, and then the stopple 4 is secured to the end of tube 1. Inner end surface of second electrode 3 is well-matched with the annular end surface at the edge of tube 1 opening 1a. The inner ends of first electrode 2 and second electrode 3 are interconnected with the liquid in the cavity 1e, and the outer ends of first electrode 2 and second electrode 3 can be electrically connected with the exterior, so the first electrode 2 and second electrode 3 are connected with the pulse power supply. Electrification produces an electric field within the cavity 1e of shock tube, causing the cell membranes to possess certain permeability, so that the target material in the liquid sample can enter the cells. In the present technical solution, when the stopple 4 is fixed to the end portion of the tube 1, the elastic piece 5 is positioned between the pipe 45 of the stopple 4 and the mounting seat 44, and the two ends of the elastic piece 5 abut against the stopple 4 and second electrode 3 respectively. The elastic piece 5 generates compressive deformation, so that the elastic piece 5 forms a seal with the stopple 4 and second electrode 3, preventing occurrence of gaps between the second electrode 3 and the opening 1a of tube 1, and inhibiting air from entering the liquid sample in cavity 1e. Further, when the stopple 4 becomes slightly uptilted, the elastic piece 5 can also make certain deformation recovery, to ensure the second electrode 3 to remain closely abutting with the end surface of opening 1a edge, so that still no air bubble will be generated in liquid sample in the cavity 1e when there is some operation deviation during sample loading by the experimenter. In summary, the technical solution can effectively improve sealing performance between second electrode 3 and opening 1a, thus inhibiting ambient air from entering the cavity 1e when loading liquid sample. Since the elastic piece 5 is positioned between the pipe 45 of the stopple 4 and mounting seat 44, and its upper and lower ends abut against the stopple 4 and second electrode 3 respectively, therefore no falling off will occur.

The tube 1 and stopple 4 in one embodiment are made of an insulating material. The first electrode 2 and second electrode 3 are made of an electrically conductive material, which is a part of the prior art, and the specific material being used are not the subject of this Specification. In addition, the first electrode 2 may either be directly fixed to the tube 1, or may be installed inside the stopple 4, as with the second electrode 3 before being used to seal the cavity 1e of tube 1.

As shown in FIG. 17, the inner side surface of one embodiment of elastic piece 5 is in contact with the outer side surface of mounting seat 44. The inner side surface of elastic piece 5 is in contact and abuts against the stopple 4, forming a multi-face seal connection. The sealing performance is further enhanced by the formation of seal connection between the lower end surface of elastic piece 5 and second electrode 3. The rim 31a is cone shape. Outer side surface of the rim 31a has a first guiding surface 31b obliquely extended towards outer side surface from end surface of rim 31a. The inner side wall of the mounting seat 44 is provided with a second guiding surface obliquely extended to inner side wall from end surface of the mounting seat 44. Through the guiding effect of first guiding surface 31b and second guiding surface, it is possible to facilitate the installation and placement of the second electrode 3.

The periphery of the opening 1a has a positioning structure which is capable of fixing the stopple 4 at the end portion of tube 1 and generating a compressive deformation to the elastic piece 5. The positioning structure comprises a connecting tube 1b which forms an integral body with the end part of the tube 1. The connecting tube 1b is provided with a chamber 1c for the stopple 4 to plug-in. The chamber wall of the chamber 1c has a first rib 1d. The outer side surface of the stopple 4 has a second rib 43 which can snap-connect with first rib 1d. Through the positioning structure, the elastic piece 5 is deformed to further improve the sealing performance, while it is also possible to effectively prevent the stopple 4 from falling off the end of tube 1. The first rib 1d and second rib 43 may be of a complete annular-shape or discontinuous annular shape or even non-annular shape. A snap-connection effect can be achieved in all cases. The protrusions of first rib 1d and second rib 43 may not be obvious. A stopple 4 of size slightly larger than the internal size of the connecting tube 1b is used to insert into the tube 1 portion, to achieve the purpose of positioning by interference fit method. The stopple 4 is snap-connected with the connecting tube 1b, making both connection and separation of the two very easy, to enhance the convenience in liquid injection and pipetting after the completion of electroporation. Of course the threaded connection method may also be used. While using threaded connection, the stopple 4 can be fixed to the connecting tube 1b by rotating it.

The second electrode 3 comprises a rod 31 and a cap 32. One end of the rod 31 is fixedly connected with cap 32. The other end of the rod 31 can be electrically connected with the exterior via an opening of the stopple 4. Furthermore, that end also has a rim 31a, which is extended radially along rod 31. The opening of the stopple 4 has an abutment surface 46 abutting against the rim 31a. The rim 31a is capable of, under deformation of the mounting seat 44 due to external load, and passing easily through the mounting seat 44, and then abuts against the abutment surface 46 at opening 1a portion of the stopple 4. After the mounting seat 44 has recovered from the deformation, the rim 31a in coordination with the abutment surface 46 to forms a limiting structure, which is capable of effectively preventing the second electrode 3 from falling off. There is a gap between outer side surface of the elastic piece 5 and inner side wall of the pipe 45 of the stopple 4. When the stopple 4 is fixed to the end of tube 1, lower end surface of elastic piece 5 abuts against upper end surface of the cap 32. There is a gap between outer circumferential surface of the cap 32 and inner side walls of pipe 45 of the stopple 4 too. The retaining of gaps at these two places can provide a certain amount of space for deformation of elastic piece 5, so that the automatic adjustment of gap closure between the stopple 4 and second electrode 3 is achieved by using the recovery force of elastic piece 5.

Embodiment 10

Figure 18:
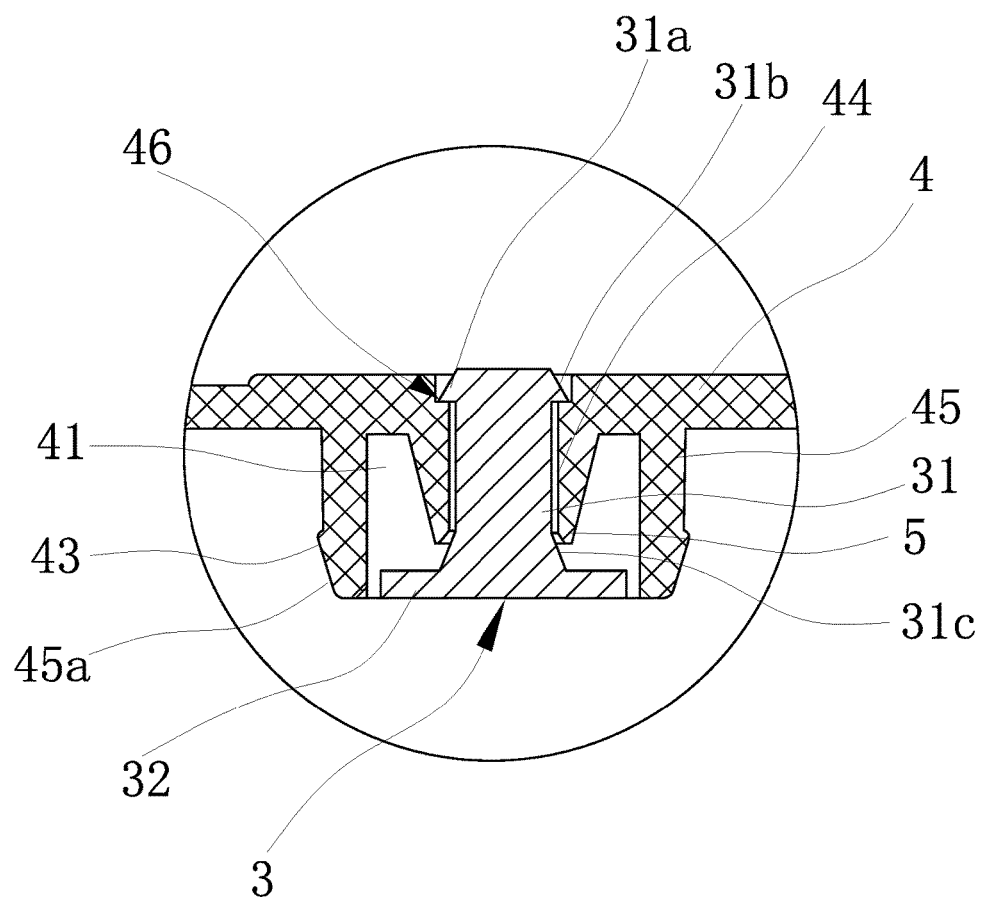
FIG. 18 is a partial enlargement diagram of embodiment 10.

As shown in FIG. 18, the present embodiment is substantially the same as Embodiment 9, except the following. In the present embodiment, the stopple 4 comprises a pipe 45 having a first through-hole 41. The rod 31 is inserted into the first through-hole 41. The pipe 45 is internally provided with a tubular mounting seat 44. The second electrode 3 is slidably connected on the mounting seat 44. The wall thickness of tubular mounting seat 44 becomes gradually thinner from top to bottom, so that the lower end portion has relatively better flexibility. The elastic piece 5 is the resilient part at lower end of the mounting seat 44. The joint of the rod 31 and cap 32 is provided with a slope 31c abutting against the elastic piece. After the slope 31c of the rod 31 is inserted into the mounting seat 44, the elastic piece 5 on the mounting seat 44 is elastically deformed to improve sealing performance and resiliency.

Embodiment 11

Figure 19:
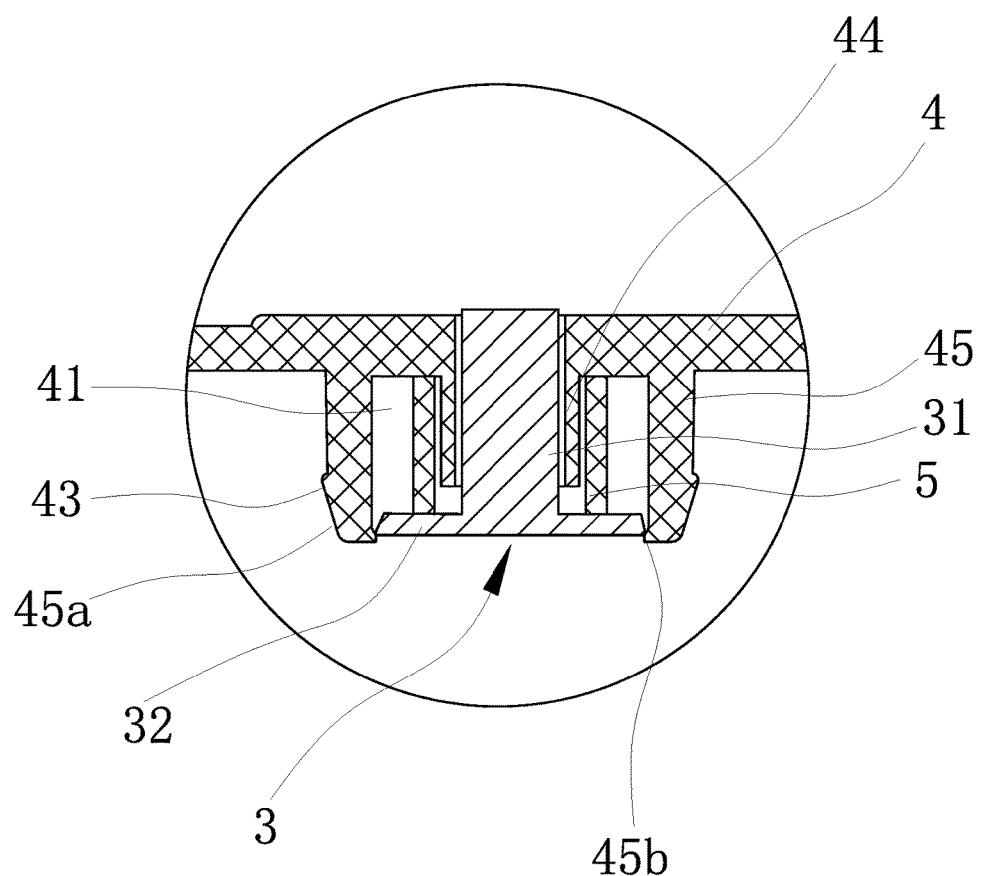
FIG. 19 is a partial enlargement diagram of embodiment 11.

As shown in FIG. 19, the present embodiment is substantially the same as Embodiment 9, except the following. The limiting structure of the present embodiment comprises an annular bulge 45b on inner wall of pipe 45. The cap 32 is disk shape, and outer diameter of the cap 32 is larger than inner diameter of the annular bulge 45b. The cap 32 can pass through the annular bulge 45b in such a way that the lower end surface of cap 32 is above the upper side surface of the annular bulge 45b. After the annular bulge 45b on pipe 45 is deformed under external compression, the cap 32 can pass smoothly through the inner hole of annular bulge 45b. After the annular bulge 45b has recovered from the deformation, the outer end surface of cap 32 abuts against the upper side surface of annular bulge 45b and maintains the limitation, effectively preventing the second electrode 3 from falling off.

Embodiment 12

Figure 20:
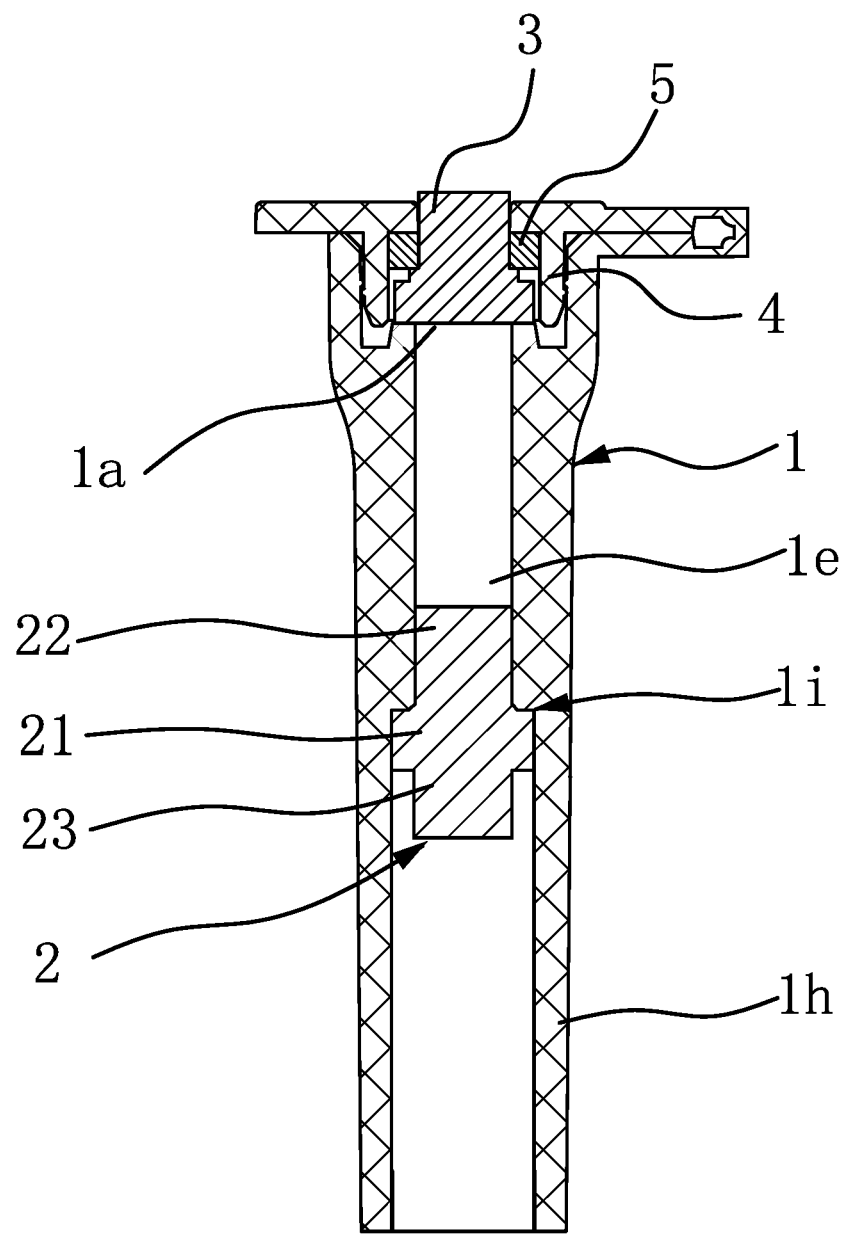
FIG. 20 is cross-sectional diagram of one embodiment of a shock tube when, together with a stopple, a second electrode is fixed in positioning structure in embodiment 12.

As shown in FIGS. 16 and 20, the present embodiment is substantially the same as Embodiments 1 to 11, except the following. The first electrode 2 is arranged at middle of the tube 1 and forms a seal with the tube 1. The first electrode 2 is acting as a divide in the tube 1. A part of it is provided with a cavity 1e for accommodating a target liquid sample. The other part of tube 1 is the extension segment 1h, which is capable of preventing the first electrode 2 and second electrode 3 from generating a high voltage arc on the outer side of the tube 1.

During operation, one embodiment of the shock tube can be filled up into the cavity 1e from opening 1a of tube 1 with a liquid sample comprising cells and materials to be injected into the cells, then the stopple 4 is secured to the end of tube 1, and inner end surface of second electrode 3 is well-matched with the annular end surface at the edge of opening 1a of tube 1. Both the first electrode 2 and second electrode 3 are interconnected with the liquid in the cavity 1e, and an electrode terminal with insulation cover can be extended into the extension segment 1h of tube 1 and electrically connected with first electrode 2, and outer end of second electrode 3 can be electrically connected with the exterior via an opening of the stopple 4, so the first electrode 2 and second electrode 3 are connected with the pulse power supply. Electrification produces an electric field within the cavity 1e of shock tube, causing the cell membranes to possess certain permeability, so that the target material in the liquid sample can enter the cells. In the present technical solution, the part of tube 1 below first electrode 2 is the extension segment 1h, which is capable of preventing the first electrode 2 and second electrode 3 from generating a high voltage arc on the outer side of the tube 1. The extension segment has good insulation performance. For the first electrode 2 and second electrode 3 to produce a high voltage arc outside the tube 1, the gap distance for voltage breakdown has been increased by at least the length of extension segment 1h or twice the length of extension segment 1h, since the arc has to bypass the extension segment 1h. The voltage breakdown gap distance between the first electrode 2 and second electrode 3 is extended greatly by the provision of extension segment 1h. Even if a very high voltage is applied, it can effectively prevent the breakdown between first electrode 2 and second electrode 3 in the ambient air of tube 1, thus ensuring the electric current to achieve electroporation to the target liquid sample in cavity 1e. In addition, the extension segment 1h is serving as a handle too, for convenience in placement and installation of the shock tube.

The lengths of extension segment 1h play a critical role. For example, when the length of extension segment 1h is greater than the length of cavity 1e, and outer side of electrode terminal is insulated, length greater than the length of cavity 1e, while the length of extension segment 1h is greater than length of cavity 1e, the air breakdown path distance between the first electrode 2 and second electrode 3 outside the tube 1 is at least three times the length of cavity 1e, hence the first electrode 2 and second electrode 3 are almost impossible to produce a high voltage arc outside the tube 1. The tube 1 is made of plastic material, and the wall thickness of tube 1 in extension segment 1h is smaller than the wall thickness of tube in the cavity 1e. The wall thickness of tube in the cavity 1e is relatively larger to prevent the high voltage breakdown between the first electrode 2 and the second electrode 3. In the meantime, the wall thickness of tube in extension segment 1h is less than the wall thickness of tube in the cavity 1e to facilitate the insertion of first electrode 2 from the extension segment 1h into the tube 1 and installed in the middle of the tube 1, and also facilitates the insertion of electrode terminal into the extension segment 1h of tube 1 to have electrical connection with the first electrode 2. The interior diameter of the tube 1 in extension segment 1h is greater than the interior diameter of the tube 1 in the cavity 1e and forms a step 1i in the tube 1. The first electrode 2 is multi-segment cylindrical or conical in shape. The first electrode 2 has a flange 21 and a peg 22 located at upper side of flange 21. The circumferential surface of flange 21 is snap-connected with the side wall of tube hole on extension segment 1h, and the end surface of the flange 21 is in contact with the step 1i. The peg 22 is snap-connected in the tube hole of the cavity 1e. The step 1i and flange 21 coordinate with each other to play a role in positioning and limitation, and to increase contact area, to improve ease of installation while ensuring sealing performance and to prevent leakage of target liquid sample. The first electrode 2 at lower side of flange 21 is provided with a contact part 23. The diameter of the contact part 23 is smaller than diameter of flange 21, and there is a gap between the contact part 23 and tube wall of extension segment 1h of the tube 1. The contact part 23 can also facilitate the handling, placement and installation of the first electrode 2. In addition, the length of the contact part 23 is shorter than the length of peg 22. The peg 22 has a longer length to facilitate installation and fixation, as well as having a better contact with the target liquid sample in cavity 1e, conducting electrical current and electric field to act on the cells in the target liquid sample. The length of the contact part is usually short, to prevent too close a distance from first electrode 2 to lower end of extension segment 1h, which may induce voltage arc, bypassing the extension segment 1h.

Further, an annular bulge is provided on the peg 22 of first electrode 2 or the flange 21 along the circumference of the first electrode 2. The annular bulge forms a tight fit seal with the inner wall of the cavity 1e. The provision of seal between annular bulge and inner wall of cavity 1e can facilitate installation and reducing resistance during the first electrode 2 placement. As an even advanced solution, if the peg 22 forms a tight fit seal with the inner wall of the cavity 1e, the outer side surface of the flange 21 and the tube wall of extension segment 1h may leave some gaps for easy installation.

The tube 1 and stopple 4 in the present embodiment are made of an insulation material. The first electrode 2 and second electrode 3 are made of an electrically conductive material, which is a part of the prior art, and the specific material being used are not the subject of this Specification. The length of extension segment 1h in the present embodiment is ⅓ ~⅔ of the total length of tube 1.

The first retaining shoulder 33 and second retaining shoulder 34 in the above embodiment may be of a complete annular-shape or composed of several arcuate segments. The simple conversion of these structural shapes is substantially identical to the present technical solution.

The description of the preferred embodiments thereof serves only as an illustration of the scope of the invention. It will be understood by those skilled in the art that various changes or supplements in form and details may be made therein without departing from the scope of the invention as defined by the appended claims.

While the present invention has been described in detail and cited with reference to specific embodiments thereof, it will be apparent to those skilled in the art that various changes and modifications may be made therein without departing from the spirit and scope of the invention.

LIST OF REFERENCE NUMERALS

1 Tube
1a Opening
1b Connecting tube
1c Chamber
1d First rib
1e Cavity
1f Annular groove
1g Ion conductive layer
1h Extension segment
1i Step
2 First electrode
20 Shock tube
3 Second electrode
4 Stopple
5 Elastic piece
6 Compression spring
7 Housing
8 Fixing base
9 Cover
10 First electrode terminal
11 Second electrode terminal
12 Hollow
13 Second through-hole
14 Spring seat
15 Spring
16 Second latch
17 Second strike
18 Retaining edge elastic piece
21 Flange
22 Peg
23 Contact part
24 Sampler
25 Micro control unit
26 Display screen
27 Power module
28 Indicator lamp
29 Sensor
30 Flexible link
31 Rod
31a Rim
31b First guiding surface
31c Slope
32 Cap
33 First retaining shoulder
34 Second retaining shoulder
41 First through-hole
42 Retaining edge
43 Second rib
44 Mounting seat
45 Pipe
45a Third guiding surface
45b Annular bulge
46 Abutment surface
81 Seat
811 Silo
82 Clamping cylinder
821 Socket
822 Handle

What is claimed is:

1. A shock tube (20), comprising:
a tube (1);
a cavity (1e) inside the tube (1), the cavity (1e) capable of accommodating a target liquid sample;
a first electrode (2) arranged at a first end of the tube (1), a working part of the first electrode (2) being interconnected with the cavity (1e);
an opening (1a) at a second end of the tube (1), the opening (1a) interconnected with the cavity (1e), an edge of the opening (1a) having an annular end surface;
a stopple (4);
a second electrode (3) arranged in the stopple (4), an outer end of the second electrode (3) capable of being electrically connected with an exterior via an opening of the stopple (4), an inner end surface of the second electrode (3) capable of being well-matched with the annular end surface of the edge of the opening (1a); and
an elastic connection in between the second electrode (3) and the stopple (4);
wherein a periphery of the opening (1a) has a positioning structure capable of fixing the stopple (4) at an end of tube (1) and rendering the second electrode (3) under elastic stress.

2. The shock tube (20) of claim 1, further comprising:
a pipe (45) of the stopple (4), the pipe (45) having a first through-hole (41);
a cap (32) of the second electrode (3);
a rod (31) of the second electrode (3), a first end of the rod (31) fixedly connected with the cap (32), a second end of the rod (31) capable of being electrically connected with the exterior via an opening of the stopple (4);
wherein the second electrode (3) is disposed in the first through-hole (41).

3. The shock tube (20) of claim 2, further comprising:
a first retaining shoulder (33) provided between the elastic piece (5) and the cap (32);

wherein a size of the first retaining shoulder (33) is larger than a diameter of rod (31) and smaller than a diameter of cap (32).

4. The shock tube (20) of claim 3,
wherein the first retaining shoulder (33) is fixedly arranged on the cap (32), and forms an integral body with the cap (32) and the rod (31); and
wherein an inner end surface of the elastic piece (5) abuts against an end surface of the first retaining shoulder (33).

5. The shock tube (20) of claim 1, wherein the elastic piece (5) is a resilient retaining edge elastic piece (18) extended inward along the first through-hole (41) on an inner wall of the first through-hole (41); and
wherein when the stopple (4) is fixed to an end of the pipe (1), the retaining edge elastic piece (18) generates deformation to press the second electrode (3) against the opening (1a).

6. The shock tube (20) of claim 1, wherein the elastic piece (5) is a compression spring (6); and
wherein when the stopple (4) is fixed to an end of the pipe (1), the compression spring (6) generates deformation to press the second electrode (3) against the opening (1a).

7. The shock tube (20) of claim 1, further comprising:
a connecting tube (1b) of the positioning structure, the connecting tube (1b) forming an integral body with an end part of the tube (1);
a chamber (1c) of the connecting tube (1b), the chamber (1c) capable of allowing the stopple (4) to plug-in;
a chamber wall of the chamber (1c), the chamber wall having a first rib (1d); and
an outer side surface of the stopple (4) having a second rib (43), the second rib (43) capable of snap-connecting with first rib (1d).

8. The shock tube (20) of claim 1,
wherein an end surface at edge of the opening (1a) has an annular groove (10.

9. The shock tube (20) of claim 1,
wherein the stopple (4) and the tube (1) is connected by a flexible link (30).

10. The shock tube (20) of claim 1,
wherein the stopple (4) and an outer side of the elastic piece (5) are well-matched and form a seal; and
wherein an inner side of the elastic piece (5) and an outer side surface of the second electrode (3) are well-matched and form a seal.

11. The shock tube (20) of claim 1,
wherein the cavity (1e) of tube (1) is provided with an ion conductive layer (1g);
wherein a bottom layer surface of the ion conductive layer (1g) is in contact with the first electrode (2); and
wherein an upper layer surface of the ion conductive layer (1g) is capable of contacting with the target liquid sample.

12. The shock tube of claim 1, further comprising:
an elastic piece (5) inside the stopple (4);
wherein when the stopple (4) is fixed to an end of the pipe (1), the elastic piece (5) generates compression deformation to press the second electrode (3) against the opening (1a).

13. A shock tube (20), comprising:
a tube (1);
a cavity (1e) inside the tube (1), the cavity (1e) capable of accommodating a target liquid sample;
a first electrode (2) arranged at a first end of the tube (1) or at a middle of the tube (1);
an opening (1a) at a second end of the tube (1), the opening (1a) interconnected with the cavity (1e);
a stopple (4);
a second electrode (3) arranged in the stopple (4);
an elastic connection in between the second electrode (3) and the stopple (4);
a rod (31) of the second electrode (3), the rod (31) inserted in the stopple (4) and slidably connected to the stopple (4);
a cap (32) of the second electrode (3), the cap (32) fixedly connected to an inner end of the rod (31);
an edge of the opening (1a) having an annular end surface, the edge of the opening (1a) capable of being well-matched with an outer end surface of the cap (32); and
a limiting structure provided between the second electrode (3) and the stopple (4), the limiting structure capable of preventing separation of the rod (31) from the stopple (4).

14. The shock tube (20) of claim 13, further comprising:
a rim (31a) of the limiting structure, the rim (31a) being on an outer end of the rod (31), the rim (31a) radially extending from the rod (31);
wherein a radial size of the rim (31a) is slightly larger than a diameter of the stopple opening; and
wherein the rim (31a) is capable of pressing the stopple (4) under external force generating deformation, causing the stopple (4) to pass out of the stopple opening.

* * * * *